(12) United States Patent
Church

(10) Patent No.: US 9,928,869 B2
(45) Date of Patent: Mar. 27, 2018

(54) METHODS FOR RETRIEVABLE INFORMATION STORAGE USING NUCLEIC ACIDS

(71) Applicant: President and Fellows of Harvard College, Cambridge, MA (US)

(72) Inventor: George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/209,127

(22) Filed: Jul. 13, 2016

(65) Prior Publication Data

US 2017/0017436 A1   Jan. 19, 2017

Related U.S. Application Data

(60) Provisional application No. 62/191,982, filed on Jul. 13, 2015.

(51) Int. Cl.
| | | |
|---|---|---|
| *G11B 7/245* | (2006.01) | |
| *C12Q 1/68* | (2018.01) | |
| *B01J 19/00* | (2006.01) | |
| *G11B 7/241* | (2006.01) | |

(52) U.S. Cl.
CPC ......... *G11B 7/245* (2013.01); *B01J 19/0046* (2013.01); *C12Q 1/6874* (2013.01); *G11B 7/241* (2013.01); *B01J 2219/00529* (2013.01); *B01J 2219/00547* (2013.01); *B01J 2219/00572* (2013.01); *B01J 2219/00596* (2013.01); *B01J 2219/00608* (2013.01); *B01J 2219/00675* (2013.01); *B01J 2219/00711* (2013.01); *B01J 2219/00713* (2013.01); *B01J 2219/00722* (2013.01)

(58) Field of Classification Search
None
See application file for complete search history.

(56) References Cited

U.S. PATENT DOCUMENTS

| | | |
|---|---|---|
| 6,312,911 B1 | 11/2001 | Bancroft et al. |
| 2003/0044781 A1 | 3/2003 | Korlach et al. |
| 2004/0001371 A1 | 1/2004 | Mansuripur et al. |
| 2004/0006433 A1 | 1/2004 | Robson et al. |
| 2005/0053968 A1 | 3/2005 | Bharadwaj et al. |
| 2007/0012783 A1 | 1/2007 | Mercolino |
| 2009/0035777 A1 | 2/2009 | Kokoris et al. |
| 2011/0119778 A1 | 5/2011 | Liss |

FOREIGN PATENT DOCUMENTS

| | | |
|---|---|---|
| CN | 1526015 A | 9/2004 |
| CN | 101965410 A | 2/2011 |
| JP | 2006-522356 A | 9/2006 |
| WO | 03/025123 A2 | 3/2003 |
| WO | 2003/064688 A2 | 8/2003 |
| WO | 2004/088585 A2 | 10/2004 |

OTHER PUBLICATIONS

Church, "Next-generation digital information storage in DNA," Science, vol. 337(6102), 2012, p. 1628 plus 16 pages of supplementary material for 18 pages total.*
C. Bancroft: "Long-Term Storage of Information in DNA". Science vol. 293. No. 5536. Sep. 7, 2001 (Sep. 7, 2001). pp. 1763c-1765. XP055082597. ISSN: 0036-8075. DOI: 10.1126jscience.293.5536.1763c the whole document.
Cox J P L: "Long-term data storage in DNA", Trends in Biotechnology, Elsevier Publications, Cambridge, GB, vol. 19, No. 7, Jul. 1, 2001 (Jul. 1, 2001), pp. 247-250, XP004246191, ISSN: 0167-7799, DOI: 10.1016/S0167-7799(01)01671-7.
G. M. Church et al: "Next-Generation Digital Information Storage in DNA". Science. vol. 337. No. 6102. Sep. 28, 2012 (Sep. 28, 2012). p. 1628-1628. XP055082578. ISSN: 0036-8075. DOI: 10.1126jscience.1226355 the whole document.
International Preliminary Report on Patentability dated Jan. 29, 2015, issued from corresponding PCT/US2013/050815, 8 pages, un-numbered.
Nick Goldman et al: "Towards practical. high-capacity. low-maintenance information storage in synthesized DNA". Nature. Jan. 1, 2013 (Jan. 1, 2013). XP055050963. ISSN: 0028-0836. DOI: 10.1038/nature11875 the whole document, pp. 1-4.
Office Action issued for corresponding Chinese Patent Application No. 201380038507.X, dated Mar. 10, 2017.
International Search Report issued from corresponding PCT/US2016/041981, dated Nov. 30, 2016.

* cited by examiner

*Primary Examiner* — G. Steven Vanni
(74) *Attorney, Agent, or Firm* — Banner & Witcoff, Ltd

(57) ABSTRACT

A method of storing information using monomers such as nucleotides is provided including converting a format of information into a plurality of bit sequences of a bit stream with each having a corresponding bit barcode, converting the plurality of bit sequences to a plurality of corresponding oligonucleotide sequences using one bit per base encoding, synthesizing the plurality of corresponding oligonucleotide sequences on a substrate having a plurality of reaction locations, and storing the synthesized plurality of corresponding oligonucleotide sequences.

17 Claims, 3 Drawing Sheets
(3 of 3 Drawing Sheet(s) Filed in Color)

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: forward universal sequencing and amplification
      primer

<400> SEQUENCE: 1
ctacacgacg ctcttccgat ct                                                  22

<210> SEQ ID NO 2
<211> LENGTH: 22
<212> TYPE: DNA
<213> ORGANISM: Artificial
<220> FEATURE:
<223> OTHER INFORMATION: reverse primer

<400> SEQUENCE: 2
agatcggaag agcggttcag ca                                                  22
```

METHODS FOR RETRIEVABLE INFORMATION STORAGE USING NUCLEIC ACIDS

RELATED APPLICATION DATA

This application claims priority to U.S. Provisional Patent Application No. 62/191,982, filed on Jul. 13, 2015 and is hereby incorporated herein by reference in its entirety for all purposes.

FIELD

The present invention relates in general to methods of using monomers, such as nucleotides, as binary bit information to encode information using sequences of the monomers, such as nucleotides, to form polymers. In this manner, the sequences of monomers, such as nucleotides, can be used to store information such as text or images or sound.

BACKGROUND

DNA has been considered as a medium for information storage. See Bancroft et al., Science 293, 1763-1765 (2001). See also, Davis, Art Journal 55, 70-74 (1996); Gustafsson, Nature 458, 703 (2009) and Gibson, Science 329, 52-56 (2010); US 2003/0228611 and WO2014/014991. See also US2010/0099080 and WO2014/014991.

SUMMARY

Embodiments of the present disclosure are directed to methods of using a polymer sequence or sequences including monomers as a medium for information storage. Certain embodiments of the present disclosure are directed to methods of using a nucleic acid sequence or sequences including nucleotides as a medium for information storage. Information is encoded in the smallest, most accurately replicated bits in nature, the base pairs themselves. Common nucleotides include adenine ("A"), cytosine ("C"), guanine ("G"), and thymine ("T"). According to certain aspects uracil ("U") can be used instead of or in addition to thymine. Additional base pairs known to those of skill in the art are contemplated, such as three base pairs for 6 bases and 6 base pairs for 12 bases. Amino acids can also be used to make polypeptides encoding information analogous to the nucleotides described herein.

Aspects of the present disclosure are directed to methods of robust, large-scale reading and writing of digital information using next generation sequencing and synthesis technologies. According to one aspect, text and/or images, and/or sound is converted to a series of bits such as megabits. According to one aspect, text and/or images and/or sound is converted to megabits comprising a bit stream. The megabits are then encoded as oligomers such as oligonucleotides. The oligomer sequences such as oligonucleotide sequences are designed and then synthesized. As an example, the oligonucleotide sequences are designed and then synthesized using enzymatic oligonucleotide synthesis reactions where an enzyme and a nucleotide are placed at a desired site on a substrate under appropriate reaction conditions and the nucleotide is covalently bound to an existing nucleotide attached to a support. The oligonucleotide sequences may be synthesized using polymerases, such as error-prone polymerases under conditions where the reagents are localized at a location on a substrate for a period of time and under such conditions to maximize probability of adding a single nucleotide. A suitable wash may also be used at a desired time to remove reagents from the location so as to minimize addition of more than one nucleotide, taking into consideration the reaction kinetics of the nucleotide addition. According to this aspect, the reagents may be added to a location on a substrate as a pulse of liquid under suitable reaction conditions and defining the time at which the nucleotide is available for addition, for example in the presence of a polymerase. Similarly, a wash may also be added to a location as a pulse of liquid to remove the reagents from the location.

According to one aspect, the oligomer, such as an oligonucleotide includes a data block sequence. According to one aspect, the oligomer, such as an oligonucleotide includes an address sequence (such as a barcode sequence) specifying the location of the data block in the bit stream. According to one aspect, the oligonucleotide includes flanking common sequences at each end of the oligonucleotide for amplification and sequencing. According to one aspect, the oligonucleotide includes one or more or all of a data block sequence, an address sequence (such as a barcode sequence) specifying the location of the data block in the bit stream, and flanking common sequences at each end of the oligonucleotide for amplification and sequencing.

According to one aspect of the present disclosure, one bit per base is encoded. According to this aspect, a single message may be encoded in a plurality of ways, i.e., A or C for zero, G or T for the number 1. Other combination are envisioned such as A or G for zero, C or T for the number 1 or A or T for zero, G or C for the number 1. Other combinations are contemplated as discussed herein. According to one aspect, the bit stream is divided into addressed data blocks. According to this aspect, a library of data blocks is created which represents the recorded information. In this manner, a single long nucleic acid sequence representing the recorded information in its entirety or comparatively long nucleic acid sequences are not required.

According to one aspect, many copies of each individual oligonucleotide are synthesized, stored and sequenced using high throughput, next-generation techniques. Since errors in synthesis and sequencing are rarely coincident, each molecular copy corrects errors in the other copies.

According to one aspect, the oligonucleotides are sequenced using methods known to those of skill in the art. For purposes of translating the nucleotide sequences into binary information bits, homopolymer runs (i.e. sequences of the same nucleotide or other monomer in series) of a particular nucleotide which may result from the use of an error-prone polymerase are treated as a single nucleotide for purposes of assigning a binary information bit, i.e. a zero or a one. According to certain other aspects, in order to distinguish between adjacent zeroes or adjacent ones in a bit stream, two monomers representative of a zero such as nucleotides A and T, for example, are alternated in the design of the oligonucleotide sequence. This allows distinguishing between adjacent zeros or ones as distinct binary information bits when homopolymer runs may result during oligonucleotide synthesis. For example, when two zeros are adjacent to one another in a bit stream, i.e. -00-, the corresponding nucleotide sequence is selected to be -AT- or -TA-. In this manner should homopolymer runs result during synthesis of the designed oligonucleotide sequence, such as -AAATTT-, the homopolymers runs will be interpreted as a single nucleotide and will be read as -AT-, corresponding to -00-. Therefore, methods of the present disclosure directed to encoding binary bit streams into nucleic acid sequences and decoding the nucleic acid sequences back into binary bit streams allows for variable nucleotide homopolymer run lengths while being able to accurately decode the nucleic acids into the binary bit stream.

According to one aspect, a method of storing information using nucleotides as representative of bits is provided comprising converting a format of information into a plurality of bit sequences of a bit stream with each having a corresponding bit barcode, converting the plurality of bit sequences to a plurality of corresponding oligonucleotide sequences using one bit per base encoding, synthesizing the plurality of corresponding oligonucleotide sequences by pulsing and synchronizing enzymatic reagents and washes so as to result in nucleotide addition to a growing oligonucleotide chain, and storing the synthesized plurality of corresponding oligonucleotide sequences. According to one aspect, the oligonucleotide sequences include one or more or all of a data block sequence, an address sequence specifying the location of the data block in the bit stream, or flanking common sequences at each end of the oligonucleotide for amplification and sequencing. According to one aspect, an error-prone polymerase may be used to synthesize the plurality of corresponding oligonucleotide sequences.

According to one aspect, a method of retrieving a format of information from a plurality of synthesized oligonucleotide sequences encoding bit sequences of the format of information is provided comprising amplifying the plurality of oligonucleotide sequences, sequencing the amplified oligonucleotide sequences, converting the oligonucleotide sequences to bit sequences by interpreting homopolymer runs as a single nucleotide, and converting the bit sequences to the format of information. According to one aspect, the oligonucleotide sequences include one or more or all of a data block sequence, an address sequence specifying the location of the data block in the bit stream, or flanking common sequences at each end of the oligonucleotide for amplification and sequencing. For purposes of translating the nucleotide sequences into binary information bits, homopolymer runs of a particular nucleotide which may result from the use of an error-prone polymerase are treated as a single nucleotide for purposes of assigning a binary information bit, i.e. a zero or a one.

According to one aspect, a method of accessing a format of information from a plurality of synthesized oligonucleotide sequences encoding bit sequences of the format of information is provided comprising amplifying the plurality of oligonucleotide sequences, sequencing the amplified oligonucleotide sequences, converting the oligonucleotide sequences to bit sequences by interpreting homopolymer runs as a single nucleotide, converting the bit sequences to the format of information, and visualizing the format of information or rendering the format of information into audio. According to one aspect, the oligonucleotide sequences include one or more or all of a data block sequence, an address sequence specifying the location of the data block in the bit stream, or flanking common sequences at each end of the oligonucleotide for amplification and sequencing. For purposes of translating the nucleotide sequences into binary information bits, homopolymer runs of a particular nucleotide which may result from the use of an error-prone polymerase are treated as a single nucleotide for purposes of assigning a binary information bit, i.e. a zero or a one.

According to one aspect, a method of storing information using nucleotides is provided comprising converting a format of information to a bit stream, encoding bit sequences into corresponding oligonucleotide sequences, synthesizing the oligonucleotide sequences for example by using an enzyme such as an error prone polymerase by pulsing and synchronizing reagents and washes so as to minimize attachment of more than one nucleotide, sequencing the oligonucleotide sequences, decoding the oligonucleotide sequences into bit sequences by interpreting homopolymer runs as a single nucleotide, assembling the bit sequences into a bit stream and converting the bit stream into the format of information. According to one aspect, the oligonucleotide sequences include one or more or all of a data block sequence, an address sequence specifying the location of the data block in the bit stream, or flanking common sequences at each end of the oligonucleotide for amplification and sequencing. For purposes of translating the nucleotide sequences into binary information bits, homopolymer runs of a particular nucleotide which may result from the use of an error-prone polymerase are treated as a single nucleotide for purposes of assigning a binary information bit, i.e. a zero or a one.

A method of storing information using nucleotides is provided comprising converting a first format of information to a first bit stream, encoding first bit sequences into corresponding oligonucleotide sequences, synthesizing the oligonucleotide sequences for example by using an error prone polymerase by pulsing and synchronizing reagents and washes so as to minimize attachment of more than one nucleotide, sequencing the oligonucleotide sequences, decoding the oligonucleotide sequences into second bit sequences by interpreting homopolymer runs as a single nucleotide, assembling the second bit sequences into a second bit stream and converting the second bit stream into a second format of information. According to one aspect, the oligonucleotide sequences include one or more or all of a data block sequence, an address sequence specifying the location of the data block in the bit stream, or flanking common sequences at each end of the oligonucleotide for amplification and sequencing. For purposes of translating the nucleotide sequences into binary information bits, homopolymer runs of a particular nucleotide which may result from the use of an error-prone polymerase are treated as a single nucleotide for purposes of assigning a binary information bit, i.e. a zero or a one.

Embodiments of the present disclosure relate to the use of molecules, such as nucleotides, as binary bits of information. The nucleotides may be representative of a binary state, such as zero or one, and sequences of nucleotides representing sequences of binary states, such as zeros or ones, may be representative of text, an image, a video or an audio format. In this manner, a written material, a picture, a video with an audio component or an audio recording or any other medium of expression, may be stored using nucleic acids as representative of bits. According to certain aspects, information to be stored is converted into binary bits, such as according to ASCII code, using a computer and appropriate software for example, which is a series of zeros and ones representative of the information. It is to be understood that the information to be stored may be converted to other coded bits of information, as is known in the art. A series of nucleotides is then determined, such as by using a computer and appropriate software, which is representative of the series of coded bits of information, such as zeros and ones. The series of nucleotides are then synthesized and stored on a storage media. When the information is to be accessed, the series of nucleotides are determined and then translated, such as by using a computer and appropriate software into a series of zeros and ones which is then translated into the information, for example using a computer and appropriate software. In this manner, aspects of the present disclosure are directed to the use of nucleic acids, whether fully- or partially single stranded, double-stranded, or multi-stranded, as storage media for information. According to one aspect, the nucleic acids are included on a support substrate whether in an ordered or random manner.

According to certain aspects, polymerases, including without limitation error-prone template-dependent polymerases, modified or otherwise, can be used to create nucleotide polymers having the desired sequence of nucleotides representing the binary bits which are representative of the information to be stored. Template-independent polymerases, whether modified or otherwise, can be used to create the nucleic acids de novo. According to one aspect, ordinary nucleotides are used, such as A, T/U, C or G. According to one aspect, nucleotides are used which lack chain terminating moieties. According to one aspect, chain terminating nucleotides are not used in the methods of making the nucleotide polymers. According to this aspect, a template independent polymerase may be used to make the nucleic acid sequence. Such template independent polymerase may be error-prone which may lead to the addition of more than one nucleotide resulting in a homopolymer. According to certain aspects of the present disclosure, homopolymer runs are interpreted as a single nucleotide for purposes of determining which binary bit of information the homopolymer run represents. Sensors, such as light activated sensors, metabolic products or chemicals, that are activated by ligands can be used with such polymerases.

The nucleic acid polymers can be sequenced using methods known to those of ordinary skill in the art. Once the nucleic acid sequence is determined, the nucleic acid sequence can be translated into a series of binary bits, i.e. zeros and ones, which can then be translated into the information represented by the series of binary bits.

Further features and advantages of certain embodiments of the present disclosure will become more fully apparent in the following description of the embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION OF CERTAIN PREFERRED EMBODIMENTS

Figure 1:
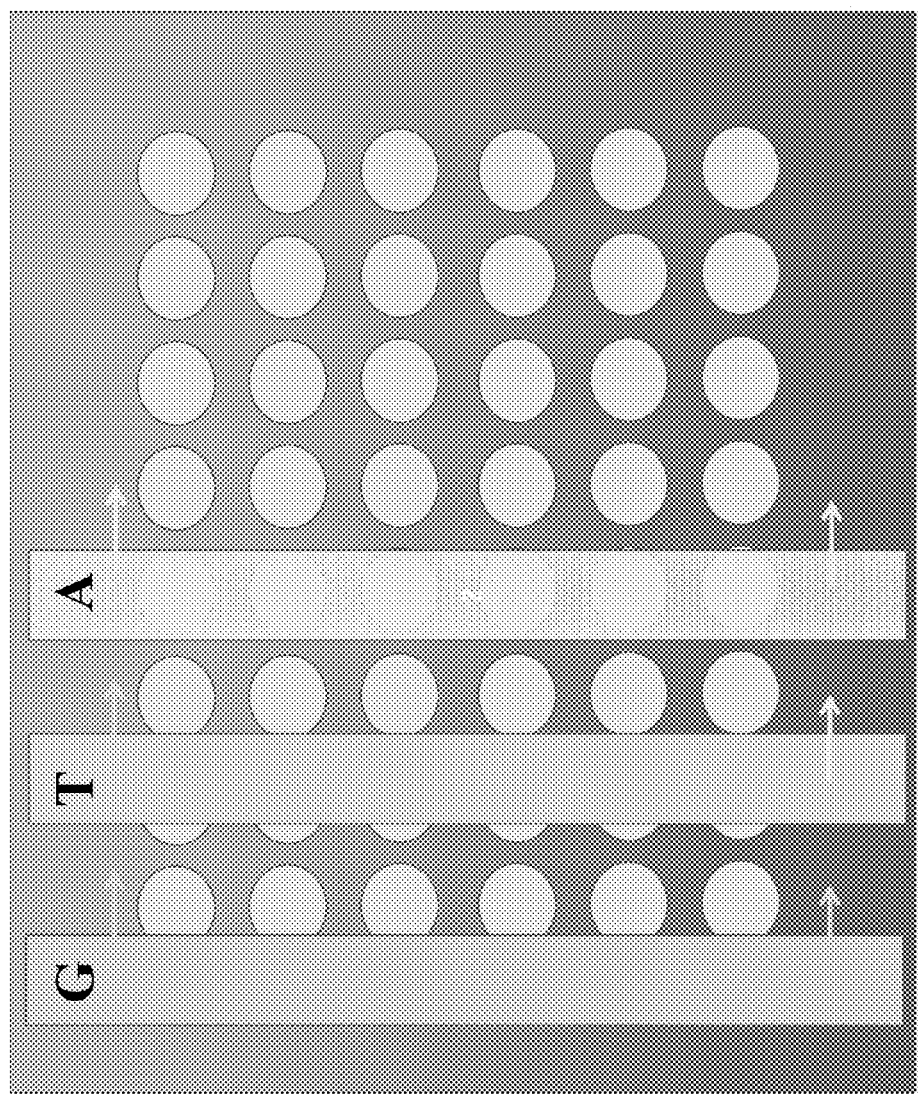
FIG. 1 is a schematic depicting pulses of nucleotides flowing across a substrate with predefined regions where oligonucleotides are to be synthesized.

The present invention is directed to methods of storing information using oligomers. Such oligomers can be formed from monomers, for example, which can represent a binary bit. Exemplary monomers include nucleotides. Exemplary oligomers include oligonucleotides. According to one aspect, a method of encoding information is provided where a sequence of bits are converted to a sequence of monomers, such as nucleotides, where the sequence of monomers is a polymer, such as an oligonucleotide. According to one aspect, methods described herein may be used for oligonucleotide synthesis or commercially available or known methods of polymer or nucleic acid synthesis may be used. According to one aspect, commercially available or known methods of nucleic acid amplification are used. According to one aspect, commercially available or known methods of nucleic acid sequencing are used. According to one aspect, commercially available or known methods of identifying monomers within a polymer are used.

According to one aspect, a portion or portions of a format of information, such as text, an image, a video or an audio format, such as an html format of information, such as an html book with text and/or images, is converted to bits, i.e. zeros and ones, for example using a computer and appropriate software, and a bit barcode is added to form a bit sequence, i.e. a series of zeros and ones as commonly understood. Other formats of information that can be converted to bits are known to those of skill in the art. According to one aspect, the portion of an html format of information to be converted into bits may be referred to as a byte portion. The bit barcode can determine the location of the encoded bits within the overall html format of information. The bit sequence is then converted (encoded), such as by a computer and appropriate software, to a designed sequence of nucleotides, i.e., an oligonucleotide or DNA or RNA using a 1 bit per base encoding (A or C=0; T/U or G=1) to form a corresponding encoded oligonucleotide sequence, i.e. the oligonucleotide sequence corresponds to or encodes for the bit sequence.

A plurality of bit sequences are created corresponding to a portion of or the entire html format of information. Accordingly, a plurality of corresponding encoded oligonucleotide sequences is created which together may be referred to as a library. The library of encoded oligonucleotide sequences represents the html format of information. According to one aspect, the oligonucleotides include a bit data block portion, a bit address portion specifying the location of the data block in the bit stream and flanking common sequences for amplification and sequencing. For example a 159 nucleotide oligonucleotide may include a 96-bit data block (96nt), a 19-bit address (19nt) and 22-bit common sequences flanking the oligonucleotide (22nt).

According to one exemplary aspect, the encoded oligonucleotide sequences are then synthesized using an error prone polymerase, such as template independent error prone polymerase, and common or natural nucleic acids, which may be unmodified. According to this aspect, initiator sequences or primers are attached to a substrate, such as a silicon dioxide substrate, at various locations whether known, such as in an addressable array, or random. Reagents including at least a selected nucleotide, a template independent polymerase and other reagents required for enzymatic activity of the polymerase are applied at one or more locations of the substrate where the initiator sequences are located and under conditions where the polymerase adds one or more than one or a plurality of the nucleotide to the initiator sequence to extend the initiator sequence. According to one aspect, the nucleotides ("dNTPs") are applied or flow in periodic applications or waves of known temporal and spatial manner or width or conditions considering the polymerase polymerization (or switching rate) rate. In this exemplary manner, blocking groups or reversible terminators are not used with the dNTPs because the reaction conditions are selected to be sufficient to limit or reduce the probability of enzymatic addition of the dNTP to one dNTP, i.e. one dNTP is added using the selected reaction conditions taking into consideration the reaction kinetics. Although, it is to be understood that nucleotides with blocking groups or reversible terminators can be used in certain embodiments. Nucleotides with blocking groups or reversible terminators are known to those of skill in the art. According to an additional embodiment when reaction conditions permit, more than one dNTP may be added to form a homopolymer run when common or natural nucleotides are used with a template independent error prone polymerase. However, during the sequencing step of the methods described herein, each homopolymer run is interpreted as representing a single dNTP. In this manner, the recording and reading methods described herein allow homopolymer runs and the synthesis methods need not add only a single dNTP, as could be the case when using template independent polymerases that may be error prone.

In addition, the present disclosure alternates between two different monomers representative of a single binary bit when making nucleic acids where the same binary bit is in series. For example, where two zeros in series, "00", are intended, the corresponding nucleic acid will have "A" represent the first zero and "C" represent the second zero, so that even if there are homopolymer runs of the As or Cs due to the error prone polymerase, the first "0" and the second "0" can be distinguished from each other as separate bits. It is to be understood that with four nucleotides, a pair of nucleotides represents a first binary bit and the remaining pair represents a second binary bit. Accordingly, A and C can represent the first binary bit and T and G represent the second binary bit. Alternatively, A and G can represent the first binary bit and T and C represent the second binary bit. Alternatively, A and T can represent the first binary bit and C and C represent the second binary bit. Alternatively, four nucleotides can be used in a "trinary" data system with three nucleotides representing 0, 1, and 2 and the remaining nucleotide being used as the next in series of the three nucleotides to distinguish between homopolymer runs. For example, with four nucleotides using a trinary data system A, C, T, can represent 0, 1, and 2 respectively and G can be used as the next in series A, C, or T to distinguish between, for example A and A in series when there may be homopolymer runs. Alternatively, three nucleotides can be used to represent a binary system where two nucleotiodes can represent 0 and 1 respectively and a third nucleotide can be used as the next in series nucleotide to distinguish between homopolymer runs.

Polymerase activity may be modified using photo-chemical or electrochemical modulation as a reaction condition so as to minimize addition of dNTP beyond a single dNTP. A wash is then applied to the one or more locations to remove the reagents. The steps of applying the reagents and the wash are repeated until desired nucleic acids are created. According to one aspect, the reagents may be added to one or more than one or a plurality of locations on the substrate in series or in parallel or the reagents may contact the entire surface of the support, such as by flowing the reagents across the surface of the support. According to one aspect, the reaction conditions are determined, for example based on reaction kinetics or the activity of the polymerase, so as to limit the ability of the polymerase to attach more than one nucleotide to the end of the initiator sequence or the growing oligonucleotide.

In addition, according to certain embodiments, polymerases can be modulated to be light sensitive for light based methods. According to this aspect, light is modulated to tune the polymerase to add only a single nucleotide. The light is shone on individual locations or pixels of the substrate where the polymerase, the nucleotide and appropriate reagents and reaction conditions are present. In this manner, a nucleotide is added to an initiator sequence or an existing nucleotide as the polymerase is activated by the light.

According to certain aspects, error prone polymerases can be used to create oligonucleotides representative of information. Such oligonucleotides are made using an error prone process. Error prone processes may include homopolymer runs, i.e. attaching two or more of a nucleotides in series, instead of attaching a single nucleotide. According to the present disclosure, the homopolymer runs are treated as being the single nucleotide of the homopolymer when sequencing the nucleic acids for translation into binary bit information.

According to certain embodiments, a template dependent error prone polymerase can be used. According to certain embodiments, a template dependent polymerase may be used which may become error prone. According to certain embodiments, a template independent RNA polymerase can be used.

In addition, useful methods of making nucleic acid sequences are disclosed in "Large-scale de novo DNA synthesis: technologies and applications," by Sriram Kosuri and George M. Church, *Nature Methods*, May, 2014, Vol. 11, No. 5, pp. 499-507 hereby incorporated by reference in its entirety.

According to certain aspects, the commercially available CustomArray system from CustomArray, Inc. is an exemplary system that can be used to make the nucleic acid sequences encoding the information to be stored by affecting or altering or producing pH locally on a substrate. It is to be understood that other methods may be used to affect or alter or produce pH at particular locations on a substrate. The CustomArray system uses a pH gradient and synthesizes a desired oligonucleotide microarray using a semiconductor-based electrochemical-synthesis process. Each oligonucleotide probe is synthesized via a platinum electrode that is independently controlled by the synthesizer's computer. According to methods described herein, a pH gradient is created which activates a pH sensitive polymerase at specific, desired locations on the substrate to add a nucleotide present in an aqueous medium at the specific, desired location. According to this aspect, pH is modulated to initiate the polymerase to add only a single nucleotide. According to aspects described herein, a system, such as the CustomArray system can be used to affect or alter or produce pH locally on a substrate where a pH dependent polymerase, a nucleotide and other suitable reagents in aqueous media are present to add the nucleotide to an initiator sequence or existing nucleotide or oligonucleotide in a method of forming an oligonucleotide. Exemplary methods described herein use aqueous solvents and pH to modulate activity of a polymerase such as a template independent polymerase, such as TdT to add a nucleotide to an existing initiator sequence, an existing nucleotide or an existing oligonucleotide at a desired location on the substrate in a method of forming an oligonucleotide.

According to one aspect, a flow cell or other channel, such a microfluidic channel or microfluidic channels having an input and an output is used to deliver fluids including reagents, such as a polymerase, a nucleotide and other appropriate reagents and washes to particular locations on a substrate within the flow cell, such as within a reaction chamber. According to certain aspects, reaction conditions are selected to selectively activate and deactivate locations on the substrate. In this manner, a desired location, such as a grid point on a substrate or array, can be provided with reaction conditions to facilitate covalent binding of a nucleotide to an initiator sequence, an existing nucleotide an existing oligonucleotide and the reaction conditions can be provided to prevent further attachment of an additional nucleotide at the same location. Then, reaction conditions to facilitate covalent binding of a nucleotide to an existing nucleotide can be provided to the same location in a method of making an oligonucleotide at that desired location.

According to one aspect, once the surface of the support has the desired nucleic acids grown thereon, a second substrate may be added to the surface of the substrate having the nucleic acids thereon and a second layer of nucleic acids may be created on the second substrate. Also, this process may be repeated for additional substrates to create a layered substrate having many or a plurality of substrate layers with nucleic acids thereon. According to this aspect, a recording medium can be made which stores information using the oligonucleotides at each layer of the recording medium.

The synthesized oligonucleotides are then amplified using methods known to those of skill in the art to form a library of oligonucleotides. The library of oligonucleotides is then sequenced using methods known to those of skill in the art, such as next-generation sequencing methods. The sequenced oligonucleotides are then converted into bit sequences corresponding to, for example, an html format of information. The bit sequences can be converted to the format of information using methods known to those of skill in the art. The format of information can be visualized or displayed or played, if an audio format, using methods and devices known to those of skill in the art.

Terms and symbols of nucleic acid chemistry, biochemistry, genetics, and molecular biology used herein follow those of standard treatises and texts in the field, e.g., Komberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

Bits

As used herein, the term "bit" is to be understood according to its common meaning to one of skill in the art. The term "bit" may be a contraction of "binary digit" and may refer to a basic capacity of information in computing and telecommunications. A "bit" represents either a first state or a second state, such as 1 or 0 (one or zero) only. The representation may be implemented, in a variety of systems, by means of a two state device.

Nucleic Acids and Nucleotides

As used herein, the terms "nucleic acid molecule," "nucleic acid sequence," "nucleic acid fragment" and "oligomer" are used interchangeably and are intended to include, but are not limited to, a polymeric form of nucleotides that may have various lengths, including either deoxyribonucleotides or ribonucleotides, or analogs thereof.

In general, the terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides (DNA) or ribonucleotides (RNA), or analogs thereof. A oligonucleotide is typically composed of a specific sequence of four nucleotide bases: adenine (A); cytosine (C); guanine (G); and thymine (T) (uracil (U) for thymine (T) when the polynucleotide is RNA). According to certain aspects, deoxynucleotides (dNTPs, such as dATP, dCTP, dGTP, dTTP) may be used. According to certain aspects, ribonucleotide triphosphates (rNTPs) may be used. According to certain aspects, ribonucleotide diphosphates (rNDPs) may be used.

The term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides. The present disclosure contemplates any deoxyribonucleotide or ribonucleotide and chemical variants thereof, such as methylated, hydroxymethylated or glucosylated forms of the bases, and the like. According to certain aspects, natural nucleotides are used in the methods of making the nucleic acids. Natural nucleotides lack chain terminating moieties. According to another aspect, the methods of making the nucleic acids described herein do not use terminating nucleic acids or otherwise lack terminating nucleic acids, such as reversible terminators known to those of skill in the art. The methods are performed in the absence of chain terminating nucleic acids or wherein the nucleic acids are other than chain terminating nucleic acids.

Examples of modified nucleotides include, but are not limited to diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A (2012) KlenTaq polymerase replicates unnatural base pairs by inducing a Watson-Crick geometry, Nature Chem. Biol. 8:612-614; See Y J, Malyshev D A, Lavergne T, Ordoukhanian P, Romesberg F E. J Am Chem Soc. 2011 Dec. 14; 133(49):19878-88, Site-specific labeling of DNA and RNA using an efficiently replicated and transcribed class of unnatural base pairs; Switzer C Y, Moroney S E, Benner S A. (1993) Biochemistry. 32(39):10489-96. Enzymatic recognition of the base pair between isocytidine and isoguanosine; Yamashige R, Kimoto M, Takezawa Y, Sato A, Mitsui T, Yokoyama S, Hirao I. Nucleic Acids Res. 2012 March; 40(6):2793-806. Highly specific unnatural base pair systems as a third base pair for PCR amplification; and Yang Z, Chen F, Alvarado J B, Benner S A. J Am Chem Soc. 2011 Sep. 28; 133(38):15105-12, Amplification, mutation, and sequencing of a six-letter synthetic genetic system. Other non-standard nucleotides may be used such as dexfribed in Malyshev, D. A., et al., Nature, vol. 509, pp. 385-388 (15 May 2014) hereby incorporated by reference in its entirety.

The 6 pairs below (A-T, G-C, Z-P, Ds-Px, NAM-SSICS, isoC-isoG) have been shown to be compatible with polymerases and orthogonal to each other (i.e. low levels of cross-pairing).

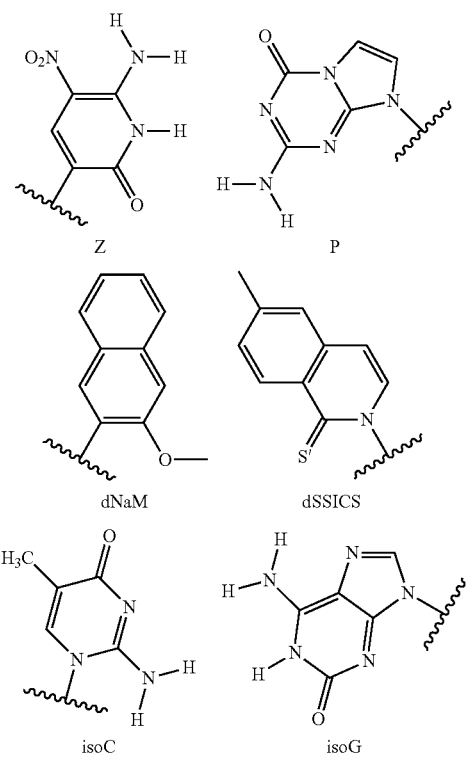

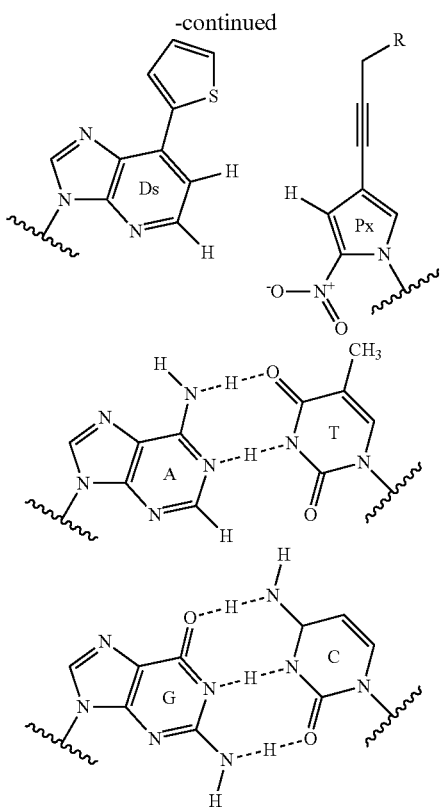

Accordingly, aspects of the present disclosure contemplate using 6 different base pairs for a 12 base system, as opposed to the two different base pairs with a four base system. Accordingly, aspects of the present disclosure contemplate using 3 different base pairs for a six base system, as opposed to the two different base pairs with a four base system.

According to one aspect, an mRNA-independent ribosome is used with pulses of tRNAs analogous to the nucleotide pulses described herein using for example the 20 standard amino acids to synthesize a polymer encoding information. This aspect provides more types of monomers—and more compact encoding, i.e. 3× bits/g due to smaller average size and 5/2× bits/g due to greater diversity of 20 standard AA plus 12 non-standard AA (5 bits) vs 4 bases (2 bits). With this embodiment, more pulses are needed per position (20 or 32 vs 4 pulses).

Non-nucleotide Monomers

Embodiments of the present disclosure include other monomer molecules which may be representative of bits and which can be formed into polymers to record information as described herein with respect to nucleotides. Such polymers and their monomers include monomers and biopolymers such as peptides and polypeptides (like collagen and vancomycin), ketides and polyketides (like fats and tetracycline), fatty acids and lipids, fatty acids and glycolipids, saccharides and lipopolysaccharides, phospholipids, hormones, polysaccharides (like cellulose and starch), terpenes and polyterpenes (like cholesterol and rubber), amino acids and polyamino-acids (like lignin and polyalkaloids), pyrroles and polypyrroles (like heme and vitamin B12), and esters and polyesters (like PHA, PHV). Additional polymers include non-biological polymers, such as linear polymers including siloxanes and polysiloxanes, acrylamides and polyacrylamides, and the like. Such oligomers may have sufficient thermal stability or ease of detection in nanopores or other polymer sequencing devices. When using non-nucleotide monomers to make polymers, methods known to those of skill in the art are used to identifying such monomers.

According to certain aspects, polymers, including non-nucleotide based polymers, identified herein may be sequenced by passing the polymer through nanopores or nanogaps or nanochannels to determine the individual monomers in the polymer. Briefly, the polymer is in an electrically conductive medium and is passed through a nanopore under the influence of a voltage differential. Interface dependent changes in ionic current are used to differentiate between individual monomers.

"Nanopore" means a hole or passage having a nanometer scale width. Exemplary nanopores include a hole or passage through a membrane formed by a multimeric protein ring. Typically, the passage is 0.2-25 nm wide. Nanopores, as used herein, may include transmembrane structures that may permit the passage of molecules through a membrane. Examples of nanopores include α-hemolysin (*Staphylococcus aureus*) and MspA (*Mycobacterium smegmatis*). Other examples of nanopores may be found in the art describing nanopore sequencing or described in the art as pore-forming toxins, such as the β-PFTs Panton-Valentine leukocidin S, aerolysin, and Clostridial Epsilon-toxin, the α-PFTs cytolysin A, the binary PFT anthrax toxin, or others such as pneumolysin or gramicidin. Nanopores have become technologically and economically significant with the advent of nanopore sequencing technology. Methods for nanopore sequencing are known in the art, for example, as described in U.S. Pat. No. 5,795,782, which is incorporated by reference. Briefly, nanopore detection involves a nanopore-perforated membrane immersed in a voltage-conducting fluid, such as an ionic solution including, for example, KCl, NaCl, NiCl, LiCl or other ion forming inorganic compounds known to those of skill in the art. A voltage is applied across the membrane, and an electric current results from the conduction of ions through the nanopore. When the nanopore interacts with polymers, such as DNA or other non-DNA polymers, flow through the nanopore is modulated in a monomer-specific manner, resulting in a change in the current that permits identification of the monomer(s). Nanopores within the scope of the present disclosure include solid state nonprotein nanopores known to those of skill in the art and DNA origami nanopores known to those of skill in the art. Such nanopores provide a nanopore width larger than known protein nanopores which allow the passage of larger molecules for detection while still being sensitive enough to detect a change in ionic current when the complex passes through the nanopore.

"Nanopore sequencing" means a method of determining the components of a polymer based upon interaction of the polymer with the nanopore. Nanopore sequencing may be achieved by measuring a change in the conductance of ions through a nanopore that occurs when the size of the opening is altered by interaction with the polymer.

In addition to a nanopore, the present disclosure envisions the use of a nanogap which is known in the art as being a gap between two electrodes where the gap is about a few nanometers in width such as between about 0.2 nm to about 25 nm or between about 2 and about 5 nm. The gap mimics the opening in a nanopore and allows polymers to pass through the gap and between the electrodes. Aspects of the present disclosure also envision use of a nanochannel electrodes are placed adjacent to a nanochannel through which the polymer passes. It is to be understood that one of skill will readily envision different embodiments of molecule or moiety identification and sequencing based on movement of a molecule or moiety through an electric field and creating a distortion of the electric field representative of the structure passing through the electric field.

Nucleic Acid Synthesis

Oligonucleotides can be made from the methods described herein using terminal deoxynucleotidyl transferase (TdT) or error-prone polymerase and/or using the pulse/synchronization methods described herein. According to certain aspects, pulses and synchronization parameters to promote the binding of a single nucleotide at a desired location can be determined based on dimensions of the substrate, reagents, concentrations, reaction temperature, and the structures used to create and deliver the pulses of regents and washes. Synchronization refers to the time a nucleotide remains at a location in the presence of an enzyme and other reactants to optimize only a single nucleotide addition, followed by a wash which can also affect the reaction rate by diluting or removing reactants from a desired location or by deactivating reagents at a desired location. According to certain aspects, pH and other reactants and reaction conditions can be optimized for the use of TdT to add a dNTP to an existing nucleotide or oligonucleotide in a template independent manner. For example, Ashley et al., Virology 77, 367-375 (1977) hereby incorporated by reference in its entirety identifies certain reagents and reaction conditions for dNTP addition, such as initiator size, divalent cation and pH. TdT was reported to be active over a wide pH range with an optimal pH of 6.85.

In certain exemplary embodiments, oligonucleotide sequences may be prepared using one or more of the phosphoramidite linkers and/or sequencing by ligation methods known to those of skill in the art. Oligonucleotide sequences may also be prepared by any suitable method, e.g., standard phosphoramidite methods such as those described herein below as well as those described by Beaucage and Carruthers ((1981) Tetrahedron Lett. 22: 1859) or the triester method according to Matteucci et al. (1981) J. Am. Chem. Soc. 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597.

According to certain aspects, oligonucleotide sequences may be prepared using ink jet techniques known to those of skill in the art, electrochemical techniques known to those of skill in the art, microfluidic techniques known to those of skill in the art, photogenerated acids known to those of skill in the art, or photodeprotected monomers known to those of skill in the art. Such techniques have the advantage of making oligonucleotides at high speed, low cost, fewer toxic chemicals, enhanced portability and ability to interleave DNA biochemistry (e.g. modifications, polymerases, hybridization etc.) with de novo (digital or analog) synthesis. For example, spatially patterned light, either directly from camera optics or from Digital Micromirror Display devices (DMD), can be used with aqueous chemistry. See US2003/0228611. For example, a template-independent polymerase like Terminal deoxynucleotidyl Transferase (TdT) or poly (A) polymerase—alternatively, a template-dependent polymerase like Taq or Phi29 derivatives, can have their basic polymerase function, base-specificity or fidelity programmable by light by incorporating an azobenzene amino acid (see Hoppmann C, Schmieder P, Heinrich N, Beyermann M. (2011) Chembiochem.12(17):2555-9. doi: 10.1002/cbic.201100578. Epub 2011 Oct. 13, Photoswitchable click amino acids: light control of conformation and bioactivity) into the active site of the polymerase or 5' to 3' exonuclease domains (if present).

Light sensitive neurons (optogenetics) can trigger ion-sensitive polymerases (see Zamft B, Marblestone A, Kording K, Schmidt D, Martin-Alarcon D, Tyo K, Boyden E, Church G M (2012) Measuring Cation Dependent DNA Polymerase Fidelity Landscapes by Deep Sequencing. PLoS One, in press) or, for some applications, the ion flux patterns themselves can constitute the stored datasets.

According to certain aspects, nucleic acids can be manufactured on substrates using electrode arrays, conventional camera optics, microscopy optics, flat optics (fresnel or bead microlens), curved imaging planes. Square, trigonal, hexagonal, or other repeating motifs (as in digital photography) arrays or analog imaging (as in conventional silver halide photography). If light is used, the spatial patterning can be via DMD (digital micro mirror device), other digital project methods or natural (analog) light fields.

According to certain aspects, nucleic acids can be made by electrochemical solid phase synthesis as disclosed in U.S. Pat. No. 6,093,302 hereby incorporated by reference in its entirety. According to this aspect, diverse sequences of separate polymers or nucleic acids sequences are prepared using electrochemical placement of monomers or nucleotides at a specific location on a substrate containing at least one electrode that is preferentially in contact with a buffering or scavenging solution to prevent chemical crosstalk between electrodes due to diffusion of electrochemically generated reagents.

According to certain aspects, photogenerated acids may be used to synthesize nucleic acids as described in Church et al., Nature, Vol. 432, 23/30 Dec. 2004 hereby incorporated by reference in its entirety.

According to certain aspects, methods of providing or delivering dNTP, rNTP or rNDP are useful in making nucleic acids. Release of a lipase or other membrane-lytic enzyme from pH-sensitive viral particoles inside dNTP filled-liposomes is described in *J Clin Microbiol.* May 1988; 26(5): 804-807. Photo-caged rNTPs or dNTPs from which NTPs can be released, typically nitrobenzyl derivatives sensitive to 350 nm light, are commercially available from Lifetechnologies. Rhoposin or bacterio-opsin triggered signal transduction resulting in vesicular or other secretion of nucleotides is known in the art. With these methods for delivering dNTPs, the nucleotides should be removed or sequestered between the first primer-polymerase encountered and any downstream.

According to certain aspects, methods of using pH or light to modulate polymerase activity is useful in making nucleic acids. Polymerases having an optimal pH range for nucleotide incorporation and a pH range in which reversible activity occurs are known in the art. Azobenzene amino acids can be incorporated into the DNA or RNA polymerases via synthetic peptides or unique genetic codes with altered tRNAs as described in ACS Nano. 2014 May 27; 8(5):4157-65. Further useful methods are described in Nature, 500(7463) Aug. 22, 2013.

Polymerases

According to an alternate embodiment of the present invention, polymerases are used to build nucleic acid molecules representing information which is referred to herein as being recorded in the nucleic acid sequence or the nucleic acid is referred to herein as being storage media. Polymerases are enzymes that produce a nucleic acid sequence, for example, using DNA or RNA as a template. Polymerases that produce RNA polymers are known as RNA polymerases, while polymerases that produce DNA polymers are known as DNA polymerases. Polymerases that incorporate errors are known in the art and are referred to herein as an "error-prone polymerases". Template independent polymerases may be error prone polymerases. Using an error-prone polymerase allows the incorporation of specific bases at precise locations of the DNA molecule. Error-prone polymerases will either accept a non-standard base, such as a reversible chain terminating base, or will incorporate a different nucleotide, such as a natural or unmodified nucleotide that is selectively given to it as it tries to copy a template. Template-independent polymerases such as terminal deoxynucleotidyl transferase (TdT), also known as DNA nucleotidylexotransferase (DNTT) or terminal transferase create nucleic acid strands by catalyzing the addition of nucleotides to the 3' terminus of a DNA molecule without a template. The preferred substrate of TdT is a 3'-overhang, but it can also add nucleotides to blunt or recessed 3' ends. Cobalt is a cofactor, however the enzyme catalyzes reaction upon Mg and Mn administration in vitro. Nucleic acid initiators may be 4 or 5 nucleotides or longer and may be single stranded or double stranded. Double stranded initiators may have a 3' overhang or they may be blunt ended or they may have a 3' recessed end.

TdT, like all DNA polymerases, also requires divalent metal ions for catalysis. However, TdT is unique in its ability to use a variety of divalent cations such as $Co^{2+}$, $Mn^{2+}$, $Zn^{2+}$ and $Mg^{2+}$. In general, the extension rate of the primer p(dA)n (where n is the chain length from 4 through 50) with dATP in the presence of divalent metal ions is ranked in the following order: $Mg^{2+} > Zn^{2+} > Co^{2+} > Mn^{2+}$. In addition, each metal ion has different effects on the kinetics of nucleotide incorporation. For example, $Mg^{2+}$ facilitates the preferential utilization of dGTP and dATP whereas $Co^{2+}$ increases the catalytic polymerization efficiency of the pyrimidines, dCTP and dTTP. $Zn^{2+}$ behaves as a unique positive effector for TdT since reaction rates with $Mg^{2+}$ are stimulated by the addition of micromolar quantities of $Zn^{2+}$. This enhancement may reflect the ability of $Zn^{2+}$ to induce conformational changes in TdT that yields higher catalytic efficiencies. Polymerization rates are lower in the presence of $Mn^{2+}$ compared to $Mg^{2+}$, suggesting that $Mn^{2+}$ does not support the reaction as efficiently as Mg2+. Further description of TdT is provided in *Biochim Biophys Acta.*, May 2010; 1804(5): 1151-1166 hereby incorporated by reference in its entirety. In addition, one may replace Mg2+, Zn2+, Co2+, or Mn2+ in the nucleotide pulse with other cations designed modulate nucleotide attachment. For example, if the nucleotide pulse replaces Mg++ with other cation(s), such as Na+, K+, Rb+, Be++, Ca++, or Sr++, then the nucleotide can bind but not incorporate, thereby regulating whether the nucleotide will incorporate or not. Then a pulse of (optional) pre-wash without nucleotide or Mg++ can be provided or then Mg++ buffer without nucleotide can be provided.

By limiting nucleotides available to the polymerase, the incorporation of specific nucleic acids into the polymer can be regulated. Thus, these polymerases are capable of incorporating nucleotides independent of the template sequence and are therefore beneficial for creating nucleic acid sequences de novo. The combination of an error-prone polymerase and a primer sequence serves as a writing mechanism for imparting information into a nucleic acid sequence.

By limiting nucleotides available to a template independent polymerase, the addition of a nucleotide to an initiator sequence or an existing nucleotide or oligonucleotide can be regulated to produce an oligonucleotide by extension. Thus, these polymerases are capable of incorporating nucleotides without a template sequence and are therefore beneficial for creating nucleic acid sequences de novo.

The eta-polymerase (Matsuda et al. (2000) Nature 404 (6781):1011-1013) is an example of a polymerase having a high mutation rate (~10%) and high tolerance for 3' mismatch in the presence of all 4 dNTPs and probably even higher if limited to one or two dNTPs. Hence, the eta-polymerase is a de novo recorder of nucleic acid information similar to terminal deoxynucleotidyl transferase (TdT) but with the advantage that the product produced by this polymerase is continuously double-stranded. Double stranded DNA has less sticky secondary structure and has a more predictable secondary structure than single stranded DNA. Furthermore, double stranded DNA serves as a good support for polymerases and/or DNA-binding-protein tethers.

According to certain aspects, a template dependent or template semi-dependent error prone polymerase can be used. According to certain embodiments, a template dependent polymerase may be used which may become error prone. According to certain embodiments, a template independent RNA polymerase can be used. Where a template dependent or template semi-dependent polymerase is used, any combination of templates with universal bases can be used which encourage acceptance of many nucleotide types. In addition, error tolerant cations such as $Mn^+$ can be used. Further, the present disclosure contemplates the use of error-tolerant polymerase mutants. See Berger et al., Universal Bases for Hybridization, Replication and Chain Termination, Nucleic Acids Research 2000, Aug. 1, 28(15) pp. 2911-2914 hereby incorporated by reference.

According to certain aspects, proteins, nucleic acids or other polymers can be attached covalently or noncovalently to a polymerase or nucleic acid or other polymer to alter the association of the polymerase and primer in a manner to alter the ability of the polymerase to add a monomer to the polymer.

According to certain aspects, DNA or RNA degrading enzymes can be reversed and are useful in making nucleic acids. One example is polynucleotide phosphorylase for making ribo-NTPs.

According to certain aspects, ligases are useful in making nucleic acids. Such ligases include DNA ligases known to those of skill in the art and RNA ligases known to those of skill in the art. DNA ligases include bacterial and mammalian DNA ligases. Exemplary ligases include T3 ligase, T4 ligase, T7 ligase, *E. coli* DNA ligase, Taq DNA ligase, circ-ligase and the like.

According to certain aspects, nucleic acids that have been synthesized on the surface of a support may be removed, such as by a cleavable linker or linkers known to those of skill in the art. The nucleic acids may be positioned on a different substrate, such as at a higher density than the manufacturing density, or on a different substrate that is to serve as the storage medium. Also, additional layers of substrates may be added which serve as new substrates for additional nucleic acid synthesis. Accordingly, methods are provided to make a high density nucleic acid storage device by generating a plurality of oligonucleotides on a first substrate, removing the plurality of oligonucleotides from the first substrate and attaching them to a second substrate in a random or ordered manner and with a desired density.

Supports and Attachment

In certain exemplary embodiments, one or more oligonucleotide sequences described herein are immobilized on a support (e.g., a solid and/or semi-solid support). In certain aspects, an oligonucleotide sequence can be attached to a support using one or more of the phosphoramidite linkers described herein. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. Supports of the present invention can be any shape, size, or geometry as desired. For example, the support may be square, rectangular, round, flat, planar, circular, tubular, spherical, and the like. When using a support that is substantially planar, the support may be physically separated into regions, for example, with trenches, grooves, wells, or chemical barriers (e.g., hydrophobic coatings, etc.). Supports may be made from glass (silicon dioxide), metal, ceramic, polymer or other materials known to those of skill in the art. Supports may be a solid, semi-solid, elastomer or gel. In certain exemplary embodiments, a support is a microarray. As used herein, the term "microarray" refers in one embodiment to a type of array that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate create a substantially planar surface. Spatially defined sites may additionally be "addressable" in that its location and the identity of the immobilized probe at that location are known or determinable.

The solid supports can also include a semi-solid support such as a compressible matrix with both a solid and a liquid component, wherein the liquid occupies pores, spaces or other interstices between the solid matrix elements. Preferably, the semi-solid support materials include polyacrylamide, cellulose, poly dimethyl siloxane, polyamide (nylon)

and cross-linked agarose, -dextran and -polyethylene glycol. Solid supports and semi-solid supports can be used together or independent of each other.

Supports can also include immobilizing media. Such immobilizing media that are of use according to the invention are physically stable and chemically inert under the conditions required for nucleic acid molecule deposition and amplification. A useful support matrix withstands the rapid changes in, and extremes of, temperature required for PCR. The support material permits enzymatic nucleic acid synthesis. If it is unknown whether a given substance will do so, it is tested empirically prior to any attempt at production of a set of arrays according to the invention. According to one embodiment of the present invention, the support structure comprises a semi-solid (i.e., gelatinous) lattice or matrix, wherein the interstices or pores between lattice or matrix elements are filled with an aqueous or other liquid medium; typical pore (or 'sieve') sizes are in the range of 100 μm to 5 nm. Larger spaces between matrix elements are within tolerance limits, but the potential for diffusion of amplified products prior to their immobilization is increased. The semi-solid support is compressible. The support is prepared such that it is planar, or effectively so, for the purposes of printing. For example, an effectively planar support might be cylindrical, such that the nucleic acids of the array are distributed over its outer surface in order to contact other supports, which are either planar or cylindrical, by rolling one over the other. Lastly, a support material of use according to the invention permits immobilizing (covalent linking) of nucleic acid features of an array to it by means known to those skilled in the art. Materials that satisfy these requirements comprise both organic and inorganic substances, and include, but are not limited to, polyacrylamide, cellulose and polyamide (nylon), as well as cross-linked agarose, dextran or polyethylene glycol.

One embodiment is directed to a thin polyacrylamide gel on a glass support, such as a plate, slide or chip. A polyacrylamide sheet of this type is synthesized as follows. Acrylamide and bis-acrylamide are mixed in a ratio that is designed to yield the degree of crosslinking between individual polymer strands (for example, a ratio of 38:2 is typical of sequencing gels) that results in the desired pore size when the overall percentage of the mixture used in the gel is adjusted to give the polyacrylamide sheet its required tensile properties. Polyacrylamide gel casting methods are well known in the art (see Sambrook et al., 1989, *Molecular Cloning. A Laboratory Manual*, 2nd Edition, Cold Spring Harbor Laboratory Press, Cold Spring Harbor, N.Y., incorporated herein in its entirety by reference), and one of skill has no difficulty in making such adjustments.

The gel sheet is cast between two rigid surfaces, at least one of which is the glass to which it will remain attached after removal of the other. The casting surface that is to be removed after polymerization is complete is coated with a lubricant that will not inhibit gel polymerization; for this purpose, silane is commonly employed. A layer of silane is spread upon the surface under a fume hood and allowed to stand until nearly dry. Excess silane is then removed (wiped or, in the case of small objects, rinsed extensively) with ethanol. The glass surface which will remain in association with the gel sheet is treated with γ-methacryloxypropyltrimethoxysilane (Cat. No. M6514, Sigma; St. Louis, Mo.), often referred to as 'crosslink silane', prior to casting. The glass surface that will contact the gel is triply-coated with this agent. Each treatment of an area equal to 1200 $cm^2$ requires 125 μl of crosslink silane in 25 ml of ethanol. Immediately before this solution is spread over the glass surface, it is combined with a mixture of 750 μl water and 75 μl glacial acetic acid and shaken vigorously. The ethanol solvent is allowed to evaporate between coatings (about 5 minutes under a fume hood) and, after the last coat has dried, excess crosslink silane is removed as completely as possible via extensive ethanol washes in order to prevent 'sandwiching' of the other support plate onto the gel. The plates are then assembled and the gel cast as desired.

The only operative constraint that determines the size of a gel that is of use according to the invention is the physical ability of one of skill in the art to cast such a gel. The casting of gels of up to one meter in length is, while cumbersome, a procedure well known to workers skilled in nucleic acid sequencing technology. A larger gel, if produced, is also of use according to the invention. An extremely small gel is cut from a larger whole after polymerization is complete.

Note that at least one procedure for casting a polyacrylamide gel with bioactive substances, such as enzymes, entrapped within its matrix is known in the art (O'Driscoll, 1976, *Methods Enzymol.*, 44: 169-183, incorporated herein in its entirety by reference). A similar protocol, using photo-crosslinkable polyethylene glycol resins, that permit entrapment of living cells in a gel matrix has also been documented (Nojima and Yamada, 1987, *Methods Enzymol.*, 136: 380-394, incorporated herein in its entirety by reference). Such methods are of use according to the invention. As mentioned below, whole cells are typically cast into agarose for the purpose of delivering intact chromosomal DNA into a matrix suitable for pulsed-field gel electrophoresis or to serve as a "lawn" of host cells that will support bacteriophage growth prior to the lifting of plaques according to the method of Benton and Davis (see Maniatis et al., 1982, *Molecular Cloning: A Laboratory Manual*, Cold Spring Harbor Laboratory Press, Cold Spring Harbor, N.Y., incorporated herein in its entirety by reference). In short, electrophoresis-grade agarose (e.g., Ultrapure; Life Technologies/Gibco-BRL) is dissolved in a physiological (isotonic) buffer and allowed to equilibrate to a temperature of 50° C. to 52° C. in a tube, bottle or flask. Cells are then added to the agarose and mixed thoroughly, but rapidly (if in a bottle or tube, by capping and inversion, if in a flask, by swirling), before the mixture is decanted or pipetted into a gel tray. If low-melting point agarose is used, it may be brought to a much lower temperature (down to approximately room temperature, depending upon the concentration of the agarose) prior to the addition of cells. This is desirable for some cell types; however, if electrophoresis is to follow cell lysis prior to covalent attachment of the molecules of the resultant nucleic acid pool to the support, it is performed under refrigeration, such as in a 4° C. to 10° C. 'cold' room.

Oligonucleotides immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. In certain exemplary embodiments, probes are immobilized via one or more cleavable linkers. The density of non-overlapping regions containing nucleic acids in a microarray is typically greater than 100 per $cm^2$, and more typically, greater than 1000 per $cm^2$. Microarray technology relating to nucleic acid probes is reviewed in the following exemplary references: Schena, Editor, Microarrays: A Practical Approach (IRL Press, Oxford, 2000); Southern, Current Opin. Chem. Biol., 2: 404-410 (1998); Nature Genetics Supplement, 21:1-60 (1999); and Fodor et al, U.S. Pat. Nos. 5,424,186; 5,445,934; and 5,744,305.

Methods of immobilizing oligonucleotides to a support are known in the art (beads: Dressman et al. (2003) Proc. Natl. Acad. Sci. USA 100:8817, Brenner et al. (2000) Nat. Biotech. 18:630, Albretsen et al. (1990) Anal. Biochem. 189:40, and Lang et al. Nucleic Acids Res. (1988) 16:10861; nitrocellulose: Ranki et al. (1983) Gene 21:77; cellulose: Goldkorn (1986) Nucleic Acids Res. 14:9171; polystyrene: Ruth et al. (1987) Conference of Therapeutic and Diagnostic Applications of Synthetic Nucleic Acids, Cambridge U.K.; teflon-acrylamide: Duncan et al. (1988) Anal. Biochem. 169:104; polypropylene: Polsky-Cynkin et al. (1985) Clin. Chem. 31:1438; nylon: Van Ness et al. (1991) Nucleic Acids Res. 19:3345; agarose: Polsky-Cynkin et al., Clin. Chem. (1985) 31:1438; and sephacryl: Langdale et al. (1985) Gene 36:201; latex: Wolf et al. (1987) Nucleic Acids Res. 15:2911). Supports may be coated with attachment chemistry or polymers, such as amino-silane, NHS-esters, click chemistry, polylysine, etc., to bind a nucleic acid to the support.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994.

According to certain aspects, affixing or immobilizing nucleic acid molecules to the substrate is performed using a covalent linker that is selected from the group that includes oxidized 3-methyl uridine, an acrylyl group and hexaethylene glycol. In addition to the attachment of linker sequences to the molecules of the pool for use in directional attachment to the support, a restriction site or regulatory element (such as a promoter element, cap site or translational termination signal), is, if desired, joined with the members of the pool. Linkers can also be designed with chemically reactive segments which are optionally cleavable with agents such as enzymes, light, heat, pH buffers, and redox reagents. Such linkers can be employed to pre-fabricate an in situ solid-phase inactive reservoir of a different solution-phase primer for each discrete feature. Upon linker cleavage, the primer would be released into solution for PCR, perhaps by using the heat from the thermocycling process as the trigger.

It is also contemplated that affixing of nucleic acid molecules to the support is performed via hybridization of the members of the pool to nucleic acid molecules that are covalently bound to the support.

Immobilization of nucleic acid molecules to the support matrix according to the invention is accomplished by any of several procedures. Direct immobilizing via the use of 3'-terminal tags bearing chemical groups suitable for covalent linkage to the support, hybridization of single-stranded molecules of the pool of nucleic acid molecules to oligonucleotide primers already bound to the support, or the spreading of the nucleic acid molecules on the support accompanied by the introduction of primers, added either before or after plating, that may be covalently linked to the support, may be performed. Where pre-immobilized primers are used, they are designed to capture a broad spectrum of sequence motifs (for example, all possible multimers of a given chain length, e.g., hexamers), nucleic acids with homology to a specific sequence or nucleic acids containing variations on a particular sequence motif. Alternatively, the primers encompass a synthetic molecular feature common to all members of the pool of nucleic acid molecules, such as a linker sequence.

Two means of crosslinking a nucleic acid molecule to a polyacrylamide gel sheet will be discussed in some detail. The first (provided by Khrapko et al., 1996, U.S. Pat. No. 5,552,270) involves the 3' capping of nucleic acid molecules with 3-methyl uridine. Using this method, the nucleic acid molecules of the libraries of the present invention are prepared so as to include this modified base at their 3' ends. In the cited protocol, an 8% polyacrylamide gel (30:1, acrylamide: bis-acrylamide) sheet 30 μm in thickness is cast and then exposed to 50% hydrazine at room temperature for 1 hour. Such a gel is also of use according to the present invention. The matrix is then air dried to the extent that it will absorb a solution containing nucleic acid molecules, as described below. Nucleic acid molecules containing 3-methyl uridine at their 3' ends are oxidized with 1 mM sodium periodate ($NaIO_4$) for 10 minutes to 1 hour at room temperature, precipitated with 8 to 10 volumes of 2% $LiClO_4$ in acetone and dissolved in water at a concentration of 10 pmol/μl. This concentration is adjusted so that when the nucleic acid molecules are spread upon the support in a volume that covers its surface evenly and is efficiently (i.e., completely) absorbed by it, the density of nucleic acid molecules of the array falls within the range discussed above. The nucleic acid molecules are spread over the gel surface and the plates are placed in a humidified chamber for 4 hours. They are then dried for 0.5 hour at room temperature and washed in a buffer that is appropriate to their subsequent use. Alternatively, the gels are rinsed in water, re-dried and stored at −20° C. until needed. It is thought that the overall yield of nucleic acid that is bound to the gel is 80% and that of these molecules, 98% are specifically linked through their oxidized 3' groups.

A second crosslinking moiety that is of use in attaching nucleic acid molecules covalently to a polyacrylamide sheet is a 5' acrylyl group, which is attached to the primers. Oligonucleotide primers bearing such a modified base at their 5' ends may be used according to the invention. In particular, such oligonucleotides are cast directly into the gel, such that the acrylyl group becomes an integral, covalently bonded part of the polymerizing matrix. The 3' end of the primer remains unbound, so that it is free to interact with, and hybridize to, a nucleic acid molecule of the pool and prime its enzymatic second-strand synthesis.

Alternatively, hexaethylene glycol is used to covalently link nucleic acid molecules to nylon or other support matrices (Adams and Kron, 1994, U.S. Pat. No. 5,641,658). In addition, nucleic acid molecules are crosslinked to nylon via irradiation with ultraviolet light. While the length of time for which a support is irradiated as well as the optimal distance from the ultraviolet source is calibrated with each instrument used due to variations in wavelength and transmission strength, at least one irradiation device designed specifically for crosslinking of nucleic acid molecules to hybridization membranes is commercially available (Stratalinker, Stratagene). It should be noted that in the process of crosslinking via irradiation, limited nicking of nucleic acid strands occurs. The amount of nicking is generally negligible, however, under conditions such as those used in hybridization procedures. In some instances, however, the method of ultraviolet crosslinking of nucleic acid molecules will be unsuitable due to nicking. Attachment of nucleic acid molecules to the support at positions that are neither 5'- nor 3'-terminal also occurs, but it should be noted that the potential for utility of an array so crosslinked is largely uncompromised, as such crosslinking does not inhibit hybridization of oligonucleotide primers to the immobilized molecule where it is bonded to the support.

Reagent Delivery Systems

According to certain aspects, reagents and washes are delivered as pulses so that the reactants are present at a desired location for a desired period of time to, for example, covalently attached dNTP to an initiator sequence or an existing nucleotide attached at the desired location. A selected nucleotide reagent liquid is pulsed or flowed over the array and is followed by a pulse of a buffer or wash that does not include the nucleotide. The duration of the pulses is determined, for example, by the reaction kinetics whether enzymatic or otherwise. The duration of the pulses can differ between nucleotide and wash or they can be the same. For example, a 0.2 second pulse is effective for both delivering the reagent and for delivering the wash. According to certain aspects, the timing of reagent delivery and wash delivery is synchronized with respect to the access of the nucleotide for reaction and the kinetics of reaction.

Figure 2:
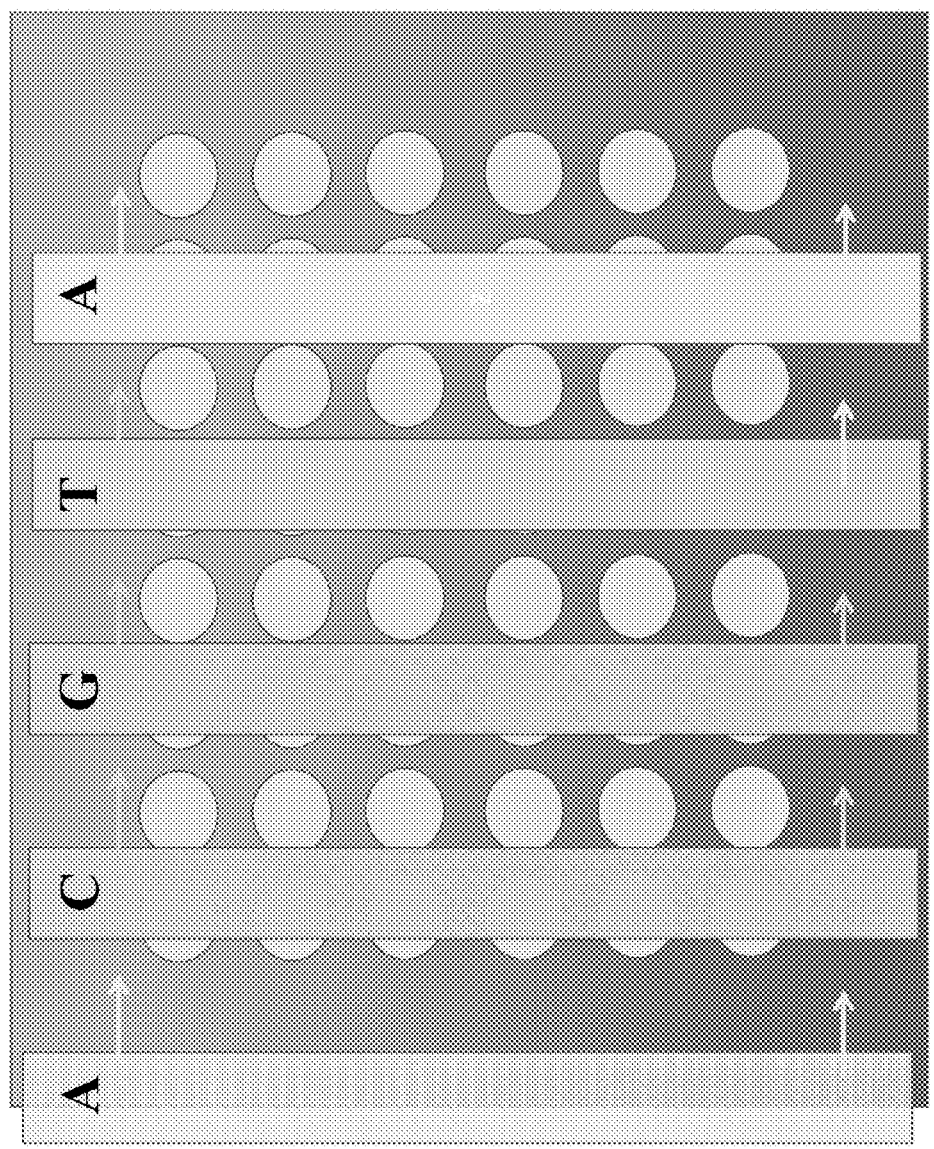
FIG. 2 is a schematic depicting pulses of nucleotides flowing across a substrate with predefined regions where oligonucleotides are to be synthesized.
Figure 3:
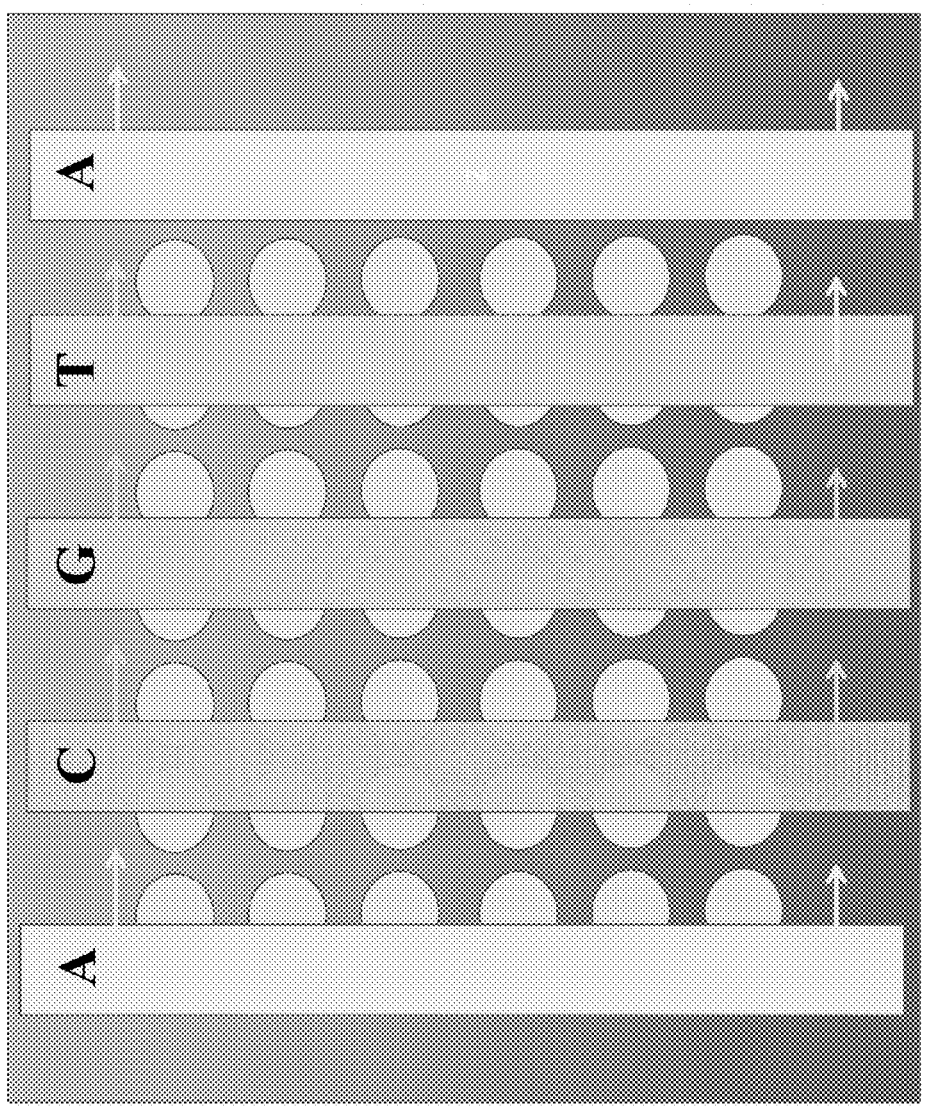
FIG. 3 is a schematic depicting pulses of nucleotides flowing across a substrate with predefined regions where oligonucleotides are to be synthesized.

For Example, with reference to FIG. 1, FIG. 2 and FIG. 3 a substrate is provided with exemplary reaction locations indicated by the circles. The reaction locations may be random or they may be predefined regions, as in an ordered array. The surface of the substrate may be enclosed to create a reaction region or a flow cell through which reactants may be flowed or the substrate may be placed within a flow cell through which reactants may be flowed. The reaction region has an input and an output so that reactants may be added and contacted to the surface of the substrate and removed. Various flow cell embodiments or flow channel embodiments or microfluidic channel embodiments are envisioned which can deliver separate reagents or a mixture of reagents or washes using pumps or electrodes or other methods known to those of skill in the art of moving fluids through channels or microfluidic channels through one or more channels to a reaction region or vessel where the surface of the substrate is positioned so that the reagents can contact the desired location where a nucleotide is to be added. The desired location can also include an electrode or other device for creating a pH or delivering a volume of fluid at a certain pH at which an enzyme will be activated or deactivated or regulated for adding a nucleotide at the desired location.

As shown in FIG. 1, a first pulse of reagents including nucleotide A is flowed across the surface of the substrate. Nucleotide A is added to one or more desired locations on the substrate where reaction conditions are sufficient for enzymatic addition of nucleotide A to an initiator sequence or an existing nucleotide or oligonucleotide. After addition of nucleotide A, a wash may be flowed across the surface of the substrate to remove nucleotide A. A second pulse of reagents including nucleotide T is then flowed across the surface of the substrate. Nucleotide T is added to one or more desired locations on the substrate where reaction conditions are sufficient for enzymatic addition of nucleotide T to an initiator sequence or an existing nucleotide or oligonucleotide. After addition of nucleotide T, a wash may be flowed across the surface of the substrate to remove nucleotide T. A third pulse of reagents including nucleotide G is then flowed across the surface of the substrate. Nucleotide G is added to one or more desired locations on the substrate where reaction conditions are sufficient for enzymatic addition of nucleotide G to an initiator sequence or an existing nucleotide or oligonucleotide. After addition of nucleotide G, a wash may be flowed across the surface of the substrate to remove nucleotide G. FIG. 2 shows a fourth pulse of reagents including nucleotide C and a fifth pulse of reagents including nucleotide A. FIG. 3 shows the pulses moving across the surface of the substrate and exiting the reaction region. According to one exemplary aspect, pH is regulated at desired locations so as to regulate the activity of the pH sensitive enzyme at the desired location to enzymatically add the nucleotide in the reagent fluid at the desired location. According to one exemplary aspect, light is regulated at desired locations so as to regulate the activity of a light sensitive enzyme at the desired location to enzymatically add the nucleotide in the reagent fluid at the desired location. Other methods of activating an enzyme by an activation stimulus are known to those of skill in the art and are useful herein to enzymatically add the nucleotide in the reagent fluid at the desired location.

According to one aspect, devices are provided that permit multiplex handling of many small pools of liquids in volumes less than 100 nanoliters. Systems for analyzing a plurality of liquid samples consisting of a platen with two parallel planar surfaces and through-holes dimensioned to maintain a liquid sample in each through-hole by surface tension are known in the art (EP 1051259A1, Nov. 15, 2000, incorporated herein in its entirety by reference). Samples can be drawn from a planar surface using capillary action and can be diluted and mixed. Each through-hole can be queried by optical radiation. This device, as well as ones like it such as the Flow-Thru Chip™ of Gene Logic (Torres et al., WO 01/45843 A2, Jun. 28, 2001, incorporated herein in its entirety by reference), is of use according to the methods described herein. The inner walls of each chamber can be functionalized with 5'-attached template nucleic acid sequences and all the other necessary reagents (such as site-specific recombinases or error-prone polymerases and nucleotides) are delivered in liquid phase to each discrete chamber (or "honeycomb" cell).

In certain embodiments, substrates such as microscope slides can be separated 1) by a wettable surface boundary area if the same pool of analyte nucleic acid molecules is intended to be evenly spread across all features on a slide or 2) by a non-wettable surface boundary area if each feature is to be spotted with a different pool of analyte nucleic acid molecules and/or primers. Combinations of the above are also possible, such as slides subdivided into larger groups of continuously wettable areas, each bounded by a non-wettable boundary, where each wettable area is further divided into smaller features each bearing different spotted primers.

According to another embodiment, it is also possible to compartmentalize single DNA molecules by dipping a slide possessing small discontinuous hydrophilic features separated by a continuous hydrophobic boundary into an aqueous solution of dilute DNA template molecules. As the slide is removed and gently blotted on its side, small beads of liquid will form over the hydrophilic features, thereby creating small discontinuous pools of liquid bearing 0, 1 or >=2 DNA template(s) (See Brennan, U.S. Pat. No. 6,210, 894 B1, Apr. 3, 2001, incorporated herein in its entirety by reference, for a description of related art).

According to another embodiment, a microfluidic device is provided with one or more reservoirs which include one or more reagents which are then transferred via microchannels to a reaction zone where the reagents are mixed and the reaction occurs. Such microfluidic devices and the methods of moving fluid reagents through such microfluidic devices are known to those of skill in the art.

Immobilized nucleic acid molecules may, if desired, be produced using a device (e.g., any commercially-available inkjet printer, which may be used in substantially unmodified form) which sprays a focused burst of reagent-containing solution onto a support (see Castellino (1997) *Genome Res.* 7:943-976, incorporated herein in its entirety by reference). Such a method is currently in practice at Incyte Pharmaceuticals and Rosetta Biosystems, Inc., the latter of which employs "minimally modified Epson inkjet cartridges" (Epson America, Inc.; Torrance, Calif.). The method of inkjet deposition depends upon the piezoelectric effect, whereby a narrow tube containing a liquid of interest (in this case, oligonucleotide synthesis reagents) is encircled by an adapter. An electric charge sent across the adapter causes the adapter to expand at a different rate than the tube, and forces a small drop of liquid reagents from the tube onto a coated slide or other support.

Reagents can be deposited onto a discrete region of the support, such that each region forms a feature of the array. The desired nucleic acid sequence can be deposited as a whole or synthesized drop-by-drop at each position, as is true for other methods known in the art. If the angle of dispersion of reagents is narrow, it is possible to create an array comprising many features. Alternatively, if the spraying device is more broadly focused, such that it disperses nucleic acid synthesis reagents in a wider angle, as much as an entire support is covered each time, and an array is produced in which each member has the same sequence (i.e., the array has only a single feature).

According to certain aspects, there are contemplated different distributions for the time for binding a nucleotide precursor (dNTP/rNTP/rNDP) and time spent in making the covalent bond with the growing primer 3' end. If the pulse of precursor is kept short then one can bind and while awaiting the covalent bond formation reaction, the ongoing flow of reagents can sweep in nucleotide depleted buffer. The first binding reaction is nucleotide concentration dependent. If a mean length of X nucleotides were the aim, then the distribution would be expected to be Poisson-distributed and the theoretical maximum for a mean of X=one nucleotide would be 37% yield, with the rest being 0, 2, 3 . . . nucleotides incorporated. In contrast, the pulsing approached described herein can result in greater than 37% yield for X=1.

According to certain aspects, an array-based, flow-cell technique is used, similar to standard synthesis and sequencing procedures. Starting TdT primers are bonded to flat silicon dioxide (or 10 micron thick polymer layer) at known locations. The dNTPs will flow in periodic waves of known temporal and spatial width adjusted to the TdT polymerization (or switching) rate. TdT activity is regulated photochemically or electrochemically, such as by altering the pH at a desired location. Locations for creating oligonucleotides can range in number between 90,000 and 5,000,000.

Exemplary methods for generating an acid or base at a known location so as to regulate pH, such as between high or low pH include at least one electrode, preferably in contact with a buffering or scavenging solution to prevent chemical crosstalk between electrodes due to diffusion of electrochemically generated reagents. See U.S. Pat. No. 6,093,302 hereby incorporated by reference. Alternatively, photo-generated acids may be used to regulate pH at a desired location. See Tian et al., Nature, Vol. 432, 23/30 Dec. 2004, pp. 1050-1054 hereby incorporated by reference.

Methods of using pH or light to modulate polymerase activity or dNTP/rNTP/rNDP access can be achieved by (1) release of lipase (or other membrane-lytic enzyme) from pH-sensitive viral particles inside (dNTP filled) liposomes (see J. Clinical Microbiology 1988 May: 26(5) 804-807) and J. Control Release 2013 Nov. 28; 172(1): 341-50; (2) Photo-caged rNTPs or dNTPs such as nitrobenzyl derivatives operative at 350 nm light; (3) Rhoposin or bacterio-opsin triggered signal transduction resulting in vesiclular or other secretion of nucleotides; (4) Polymerases having an optimal pH range for incorporation and a pH range in which reversible inactivity occurs; (5) Azobenzene amino acids incorporated into the DNA or RNA polymerase (via synthetic peptides or novel genetic codes with altered tRNAs) (see ACS Nano 2014 May 27; 8(5): 4157-65) and (6) methods described in Konerman et al., Nature (2013), Optical Control of mammalian Endogenous Transcription. According to one aspect, release of nucleotides described using methods (1)-(3) requires methods to remove or sequester released nucleotides between the first primer-polymerase encountered and any downstream. The polymerase modulation approaches (4)-(6) do not require such activities.

According to certain aspects, RNA polymerases or reversal of DNA or RNA degrading enzymes—for example, Polynucleotide phosphorylase (PNP) for ribo-NTPs, ligases such as RNA ligase, circ-ligase are contemplated. In addition to template independent polymerases, semi-dependent polymerases (aka error-prone or bypass polymerases) are contemplated. Protein, nucleic acid or other polymer rings can be attached covalently or non-covalently to the polymerase and surrounding a nucleic acid or other polymer track such that the association of the polymerase with the primer is more processive.

Amplification

In general, "amplifying" includes the production of copies of a nucleic acid molecule via repeated rounds of primed enzymatic synthesis. "In situ" amplification indicates that the amplification takes place with the template nucleic acid molecule positioned on a support or a bead, rather than in solution. In situ amplification methods are described in U.S. Pat. No. 6,432,360. Varied choices of polymerases exist with different properties, such as temperature, strand displacement, and proof-reading. Amplification can be isothermal and in similar adaptation such as multiple displacement amplification (MDA) described by Dean et al., Comprehensive human genome amplification using multiple displacement amplification, *Proc. Natl. Acad. Sci. U.S.A.*, vol. 99, p. 5261-5266. 2002; also Dean et al., Rapid amplification of plasmid and phage DNA using phi29 DNA polymerase and multiply-primed rolling circle amplification, *Genome Res.*, vol. 11, p. 1095-1099. 2001; also Aviel-Ronen et al., Large fragment Bst DNA polymerase for whole genome amplification of DNA formalin-fixed paraffin-embedded tissues, *BMC Genomics*, vol. 7, p. 312. 2006. Amplification can also cycle through different temperature regiments, such as the traditional polymerase chain reaction (PCR) popularized by Mullis et al., Specific enzymatic amplification of DNA in vitro: The polymerase chain reaction. *Cold Spring Harbor Symp. Quant. Biol.*, vol. 51, p. 263-273. 1986. Variations more applicable to genome amplification are described by Zhang et al., Whole genome amplification from a single cell: implications for genetic analysis, *Proc. Natl. Acad. Sci. U.S.A.*, vol. 89, p. 5847-5851. 1992; and Telenius et al., Degenerate oligonucleotide-primed PCR: general amplification of target DNA by a single degenerate primer, *Genomics*, vol. 13, p. 718-725. 1992. Other methods include Polony PCR described by Mitra and Church, In situ localized amplification and contact replication of many individual DNA molecules, *Nuc. Acid. Res.*, vol. 27, pages e34. 1999; emulsion PCR (ePCR) described by Shendure et al., Accurate multiplex polony sequencing of an evolved bacterial genome, *Science*, vol. 309, p. 1728-32. 2005; and Williams et al., Amplification of complex gene libraries by emulsion PCR, *Nat. Methods*, vol. 3, p. 545-550. 2006. Any amplification method can be combined with a reverse transcription step, a priori, to allow amplification of RNA. According to certain aspects, amplification is not absolutely required since probes, reporters and detection systems with sufficient sensitivity can be used to allow detection of a single molecule using template non-hybridizing nucleic acid structures described. Ways to adapt sensitivity in a system include choices of excitation sources (e.g. illumination) and detection (e.g. photodetector, photomultipliers). Ways to adapt signal level include probes allowing stacking of reporters, and high intensity reporters (e.g. quantum dots) can also be used.

Amplification methods useful in the present disclosure may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277: 7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

In exemplary embodiments, the methods disclosed herein utilize PCR amplification. "Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 68-78° C. The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 µL. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., Nucleic Acids Research, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) Anal. Biochem., 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., Biotechniques, 26:112-126 (1999); Becker-Andre et al., Nucleic Acids Research, 17:9437-9447 (1989); Zimmerman et al., Biotechniques, 21:268-279 (1996); Diviacco et al., Gene, 122:3013-3020 (1992); Becker-Andre et al., Nucleic Acids Research, 17:9437-9446 (1989); and the like.

Rolling Circle Amplification (RCA) (Zhong (2001) Proc. Natl. Acad. Sci. USA 98(7):3940-3945) represents an alternative to polony amplification since it is continuous replication and does not require thermal cycling. With only one primer (or nick), it grows one long tail from the original circle at a rate linear with time. Isothermal amplification of a circular or linear nucleic acid template also can be performed according to Tabor and Richardson (WO 00/41524) using methods in which enzymatic synthesis of nucleic acid molecules occurs in the absence of oligonucleotide primers. When a second primer from the opposite strand is also included,—highly branched structures are produced,—with mass growing initially exponentially with respect to time ($m=k*exp(t)$, or at least $m=kt^2$).

Modeling of the RCA process described herein indicates a way to build up layers in a 3D array as a function of time, chemicals and optical patterns. If replication begins in a uniform layer on the flat surface of a glass slide (or other surface), then the polymerization reaction can only occur in the next nm thick layer up. The strand-displacing activities of polymerases (such as etaPol or an eta-like BstPol) in RCA requires either nicks or primers to initiate strand-displacing DNA synthesis. If some of the RCA primers are immobilized then the hyperbranched-DNA products will be quite stable in space and time. A coarse (micron-scale, 5 Hz) pattern can be set by the megapixel micro-mirror optics, while finer detail (nm, 250 Hz) is provided by either a free running or RNAPol-etaDNAPol-fusion stepper. Nano-scale recording is not necessarily "redundant" nor limited by the micron scale light patterns, since it contains time components. The thickness, and therefore the recording capacity, would be effected by the spatiotemporal precision of specific NTP and/or dNTP pulses used for positioning and recording respectively.

In a preferred embodiment, the layers deposited can include a variety of chemistries attached to (or placed by) the nucleic acids. In one aspect, redox-sensitive fluorophore "side-chains" have been developed for each of the four dNTPs. In another aspect, photosensitive versions of each of the four dNTPs can be developed using methods known to those of skill in the art (Rob Mitra, unpublished data (2000)). In yet another aspect, metal binding groups and wires (Braun (1998) Nature 391(6669):775-778), quantum dots (Michler (2000) Nature 406(6799):968-70), quantum-wires (Emiliani (2001) J. Microsc. 202(Pt 1):229-240), magnetic dots (Cowburn (2000) Science 287(5457):1466-1468), or refractive dots (Yguerabide (1998) Anal. Biochem. 262(2):157-76), can be assembled by this method. The 3D arrays of the present invention provide fast electronic-optical pathways based on signal coincidences and/or traffic levels (analogous to learning and computing in neural circuits). The naturally hyperbranched structures found in RCA are a first step in this direction.

The de novo polymers can be stored and read with or without polymerase amplification. Amplification can be via thermal cycling or isothermal. The amplicons can be short (100 to 200 mers as is convenient for current chemical synthesis or up to 1 Mbp as might be achievable with polymerases.

Sequencing

The nucleotide type incorporated can be determined by: a) the intersection of a light pulse coincident with a particular dNTP (or rNTP or other monomer class) present at that time point in a cyclic pattern of dNTP solutions. b) 'caged' (i.e. photo-activatable or photo-inactivatable) dNTPs, rNTPs or cations. c) base-specific, light-modulated steric or conformational selectivity (see Hoppmann C, Schmieder P, Heinrich N, Beyermann M. (2011) Chembiochem.12(17):2555-9. doi: 10.1002/cbic.201100578. Epub 2011 Oct. 13. Photoswitchable click amino acids: light control of conformation and bioactivity). Poly(A) polymerase is particularly useful since its specificity for ATp relative to other rNTPs is due to a conformational change which can be mimicked by a photo-sensitive amino acid linkage (like azobenzene, with or without crosslinking).

Methods described herein are capable of generating large amounts of data (billions of bits). Accordingly, high throughput methods of sequencing these nucleic acid molecules, such as that disclosed in Mitra (1999) *Nucleic Acids Res.* 27(24):e34; pp. 1-6, are useful. In preferred embodiments, high throughput methods are used with PCR amplicons or other nucleic acid molecules having lengths of less than 100 bp. In other preferred embodiments, PCR amplicons of 100 bp, 110 bp, 120 bp, 130 bp, 140 bp, 150 bp, 160 bp, 170 bp, 180 bp, 190 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 950 bp, 1000 bp or more may be used.

Rolling Circle Amplification (RCA) (Zhong (2001) *Proc. Natl. Acad. Sci. USA* 98(7):3940-3945) represents an alternative to polony amplification since it is continuous replication and does not require thermal cycling. With only one primer (or nick), it grows one long tail from the original circle at a rate linear with time. Isothermal amplification of a circular or linear nucleic acid template also can be performed according to Tabor and Richardson (WO 00/41524) using methods in which enzymatic synthesis of nucleic acid molecules occurs in the absence of oligonucleotide primers.

Sequencing methods useful in the present disclosure include Shendure et al., Accurate multiplex polony sequencing of an evolved bacterial genome, *Science*, vol. 309, p. 1728-32. 2005; Drmanac et al., Human genome sequencing using unchained base reads on self-assembling DNA nanoarrays, *Science*, vol. 327, p. 78-81. 2009; McKernan et al., Sequence and structural variation in a human genome uncovered by short-read, massively parallel ligation sequencing using two-base encoding, *Genome Res.*, vol. 19, p. 1527-41. 2009; Rodrigue et al., Unlocking short read sequencing for metagenomics, *PLoS One*, vol. 28, e11840. 2010; Rothberg et al., An integrated semiconductor device enabling non-optical genome sequencing, *Nature*, vol. 475, p. 348-352. 2011; Margulies et al., Genome sequencing in microfabricated high-density picolitre reactors, *Nature*, vol. 437, p. 376-380. 2005; Rasko et al. Origins of the *E. coli* strain causing an outbreak of hemolytic-uremic syndrome in Germany, *N. Engl. J. Med.*, Epub. 2011; Hutter et al., Labeled nucleoside triphosphates with reversibly terminating aminoalkoxyl groups, *Nucleos. Nucleot. Nucl.*, vol. 92, p. 879-895. 2010; Seo et al., Four-color DNA sequencing by synthesis on a chip using photocleavable fluorescent nucleotides, *Proc. Natl. Acad. Sci. USA.*, Vol. 102, P. 5926-5931 (2005); Olejnik et al.; Photocleavable biotin derivatives: a versatile approach for the isolation of biomolecules, *Proc. Natl. Acad. Sci. U.S.A.*, vol. 92, p. 7590-7594. 1995; U.S. Pat. No. 5,750,34; US 2009/0062129 and US 2009/0191553.

Sequencing primers according to the present disclosure are those that are capable of binding to a known binding region of the target polynucleotide and facilitating ligation of an oligonucleotide probe of the present disclosure. Sequencing primers may be designed with the aid of a computer program such as, for example, DNAWorks, or Gene2Oligo. The binding region can vary in length but it should be long enough to hybridize the sequencing primer. Target polynucleotides may have multiple different binding regions thereby allowing different sections of the target polynucleotide to be sequenced. Sequencing primers are selected to form highly stable duplexes so that they remain hybridized during successive cycles of ligation. Sequencing primers can be selected such that ligation can proceed in either the 5' to 3' direction or the 3' to 5' direction or both. Sequencing primers may contain modified nucleotides or bonds to enhance their hybridization efficiency, or improve their stability, or prevent extension from a one terminus or the other.

According to one aspect, single stranded DNA templates (ssDNA) are prepared by RCA to be used with sequencing primers. Alternatively single stranded template is attached to beads or nanoparticles in an emulsion and amplified through ePCR. The result is clonal beads with a single amplified ssDNA template.

For the purpose of identifying several template nucleotide sequences in parallel, the templates are diluted in PBS buffer pH 7.4, and either bound to a patterned or non-patterned substrate utilizing various attachment methods, such as Biotin-Strepavidin, azide-alkyle (e.g. click chemistry), NHS-ester or Silanization (e.g. aldehyde-, epoxy-, amino-silane). According to one aspect, rolonies are attached to a patterned surface, such as a SiO2 solid surface, treated with 1% aminosilane (v/v) and let to interact for a period of time (typically between 5 minutes to 2 hours). Any unbound templates are then washed away using Wash 1 buffer.

Next, a sequencing primer is prepared and hybridized to the sequencing primer hybridizing site. According to certain aspects, sequencing primers can be prepared which can hybridize to a known sequence of the template. Alternatively, during template preparation, adapters with a known nucleic acid sequence are added to the unknown nucleic acid sequence by way of ligation, amplification, transposition or recombination according to methods known to those of skill in the art and described herein. Still alternatively, sequencing primers having a certain level of degeneracy could be used to hybridize to certain positions along the template. According to one aspect, primer degeneracy is used to allow primers to hybridize semi-randomly along the template. Primer degeneracy is selected based on statistical methods known to those of skill in the art to facilitate primers hybridizing at certain intervals along the length of the template. According to this aspect, primers can be designed having a certain degeneracy which facilitates binding every N bases, such as every 100 bases, every 200 bases, every 2000 bases, every 100,000 bases. The binding of the primers along the length of the template is based on the design of the primers and the statistical likelihood that a primer design will bind about every N bases along the length of the template. Since the sequencing primer P1 will be extended by ligation, the terminal group of the sequencing primer is typically synthesized to be ready to be covalently joined to the oligonucleotide probe by the DNA ligase. If the ligation occurs between the 5' end of the sequencing primer and the 3' end of the oligonucleotide probe, a phosphate group (5'-PO4) must be present on the sequencing primer while a hydroxyl group (3'-OH) on the oligonucleotide probe, and vice-versa. To hybridize the sequencing primer to the sequencing primer hybridizing site, 1 uM of the sequencing primer diluted in 5×SSPE buffer is used. The mixture is then incubated for a few minutes above room temperature to encourage proper annealing (typically between 1 to 5 minutes, at temperature between 25 and 55° C.).

Encoding an HTML File into DNA Segments

According to certain aspects, information such as text may be converted into HTML format (with embedded jpg images) and then read in bit form. Individual bits are converted to A or C for zero and T or G for 1. Addresses of the bitstream are 19 bits long and numbered consecutively, such as starting from 0000000000000000001. The following program identified as Bits2DNA.pl is used to encode a HTML file into DNA segments.

```
# cd "\Perl\gmc\Bin_DNA"
# "\Perl\bin\perl Bits2DNA.pl GMC Jul-2011 & May 27, 2012
# docstore.mik.ua/orelly/perl/cookbook/ch02_05.htm (bin) ch01_05.htm (char)
# http://perldoc.perl.org/functions/pack.html rand.html
# Each oligo is L(19)+8N(12)= 115 bp, long flanked by 22-mer amplification primers.
# DNA Encoded Artifacts Registry (DEAR) to coordinate global standards.
open IN, "in.html"; open OUT,">Bits2DNA.txt"; binmode IN;
$t{"0"}="a"; $t{"1"}="G"; # lowercase a,c = zero bit.
$t{"a"}="c"; $t{"G"}="T"; $t{"c"}="a"; $t{"T"}="G";
$u1=""; $u2=""; $u3=""; # Initialize; keep homopolymer runs < 4
$N=12; # Length of segment in bytes (not including segment number)
$L=19; # 2^19 = 524,288 = max number of oligos L=00010011
$seed=2; srand($seed); # remove this line to get a random seed
print int2bp(262144)," ",int2bp(262145);
$f="CTACACGACGCTCTTCCGATCT";    (SEQ ID NO. 1) # forward 'universal' sequencing & amplification primer
$r="AGATCGGAAGAGCGGTTCAGCA";   (SEQ ID NO. 2) # reverse 22-mer primer
$n=0; print OUT $f,int2bp(0)," ";   ###
while (read (IN, $text, 65536)) {
        @ascii_num = unpack("C*", $text);
    foreach $val (@ascii_num) {
        print OUT byt2bp($val);        ###
        $n++;
        if($n%$N==0){
           print OUT $r,"\n",$f,int2bp($n/$N),""; ###
        } # N bases per output line
    } # each byte
} # 65 Kbytes
for ($k=$n%$N; $k<$N; $k++){
   print OUT byt2bp(int(rand(256)));    ###
} # pad last data line to keep all oligos same size.
   print OUT "$\n";                    ###
sub byt2bp { # convert rightmost 8 bits (MSB first byte) to 8 bp
  my $b = unpack("B32", pack("N", shift));
  $p="";
  for ($i=24; $i<=31; $i++){
     $x=substr($b,$i,1); # bits 24 to 31 inclusive
     $u=$t{$x};
     if(rand(2)<1){$u=$t{$u}; } # pick synonym a=c; G=T
     if(($u eq $u1) && ($u eq $u2) && ($u eq $u3)){$u=$t{$u};}
     $u1=$u2; $u2=$u3; $u3=$u; # Shift previous base string
     $p =$p.$u;
  }
  return $p;
}
```

```
sub int2bp { # convert rightmost $L bits of 32 bit integers to $L bp
    my $b = unpack("B32", pack("N", shift));
    $p="";
    for ($i=31; $i>=32-$L; $i--) {
        $x=substr($b,$i,1); # bits 31 to $L
        $u=$t{$x};
        if(rand(2)<1){$u=$t{$u}; } # pick synonym a=c; G=T
        if(($u eq $u1) && ($u eq $u2) && ($u eq $u3)){$u=$t{$u};}
        $u1=$u2; $u2=$u3; $u3=$u; # Shift previous base string
        $p =$p.$u;
    }
    return $p;
}
buildConsensus.py
import sys
#builds consensus sequence from individual base counts
def getConsensus(finalbuckets):
    sequence = ''
    for i in range(len(finalbuckets)):
        letterindex = finalbuckets[i].index(max(finalbuckets[i]))
        if letterindex == 0:
            sequence += 'A'
        elif letterindex == 1:
            sequence += 'C'
        elif letterindex == 2:
            sequence += 'G'
        elif letterindex == 3:
            sequence += 'T'
    return sequence
oligolength = 115
currentbarcode = ''
#initialize vector to building consensus
buckets = [[0 for col in range(4)] for row in range(oligolength)]
for line in sys.stdin:
    splitline = line.split( )
    count = int(splitline[0])
    barcode = splitline[1]
    sequence = splitline[2]
    if not barcode == currentbarcode:
        if not currentbarcode == '':
            print getConsensus(buckets)
        buckets = [[0 for col in range(4)] for row in range(oligolength)]
        currentbarcode = barcode
    for i in range(oligolength):
        if sequence[i] == 'A':
            buckets[i][0] += count
        elif sequence[i] == 'C':
            buckets[i][1] += count
        elif sequence[i] == 'G':
            buckets[i][2] += count
        elif sequence[i] == 'T':
            buckets[i][3] += count
#print final consensus
print getConsensus(buckets)
```

The practice of the methods disclosed herein may employ conventional biology methods, software, computers and computer systems. Accordingly, the methods described herein may be computer implemented methods in whole or in part. Computer software utilized in the methods of the present disclosure include computer readable medium having computer-executable instructions for performing logic steps of the method of the invention. Suitable computer readable medium include, but are not limited to, a floppy disk, CD-ROM/DVD/DVD-ROM, hard-disk drive, flash memory, ROM/RAM, magnetic tapes, and others that may be developed. The computer executable instructions may be written in a suitable computer language or combination of several computer languages. The methods described herein may also make use of various commercially available computers and computer program products and software for a variety of purposes including translating text or images into binary code, designing nucleic acids sequences representative of the binary code, analyzing sequencing data from the nucleic acid sequences, translating the nucleic acid sequence data into binary code, and translating the binary code into text or images.

Embodiments of Certain Methods

Embodiments of the present disclosure include a method of creating a binary encoded polymer is provided including the steps of repeatedly extending a growing polymer chain with an extension product of (i) one or more than one of either a first monomer or a second monomer of a first monomer pair, or (ii) one or more than one of either a first monomer or a second monomer of a second monomer pair, and wherein the extension product represents a binary information bit corresponding to a bit stream translated from text or an image or a video or an audio format and wherein the first monomer and the second monomer of the first monomer pair each is representative of a first binary information bit, and wherein the first monomer and the second monomer of the second monomer pair each is representative of a second binary information bit, and alternating between the first monomer and second monomer of a given monomer pair when the extension products are representative of the same binary information bit and occur directly in series, and wherein the binary encoded polymer encodes the text or image or video or audio format. According to one aspect, the polymer is a nucleic acid. According to one aspect, the first monomer or the second monomer of the first monomer pair is a nucleotide. According to one aspect, the first monomer or the second monomer of the second monomer pair is a nucleotide. According to one aspect, the first monomer pair includes adenine (A) and thymine (T) or uracil (U). According to one aspect, the second monomer pair includes cytosine (C) and guanine (G). According to one aspect, the extension products are formed using an enzyme and a selected monomer under conditions to catalyze addition of the selected monomer. According to one aspect, the extension products are formed using a polymerase and a selected monomer under conditions to catalyze addition of the selected monomer. According to one aspect, the extension products are formed using a template independent polymerase and a selected monomer under conditions to catalyze addition of the selected monomer. According to one aspect, the growing polymer chain is attached to a substrate. According to one aspect, a plurality of growing polymer chains formed from steps (i) and (ii) are provided. According to one aspect, a plurality of growing polymer chains formed from steps (i) and (ii) is provided and wherein the plurality of growing polymer chains is attached to a substrate. According to one aspect, the first monomer or the second monomer of the first monomer pair is a natural nucleotide. According to one aspect, the first monomer or the second monomer of the second monomer pair is a natural nucleotide. According to one aspect, the first and second monomer pairs include natural nucleotides and the extension product is made by catalyzing the addition of a natural nucleotide under conditions sufficient to add a single nucleotide or more than one nucleotide. According to one aspect, the first and second monomer pairs include natural nucleotides and the extension product is made by alternating at one or more locations on the substrate administration of a polymerase and a selected nucleotide with a nucleotide deficient buffer to catalyzing the addition of a natural nucleotide under conditions sufficient to add the nucleotide.

According to one aspect, a method of creating a binary encoded polymer is provided including the steps of repeatedly extending a growing polymer chain with an extension product of (i) one or more than one of either a first monomer or a second monomer of a first monomer pair, or (ii) one or more than one of either a first monomer or a second monomer of a second monomer pair, and wherein the extension product represents a binary information bit corresponding to a bit stream translated from text or an image or a video or an audio format and wherein the first monomer and the second monomer of the first monomer pair each is representative of a first binary information bit, and wherein the first monomer and the second monomer of the second monomer pair each is representative of a second binary information bit, and alternating between the first monomer and second monomer of a given monomer pair when the extension products are representative of the same binary information bit and occur directly in series, and wherein the extension product includes at least one homopolymer of either the first monomer or the second monomer of the first monomer pair or at least one homopolymer of either the first monomer or the second monomer of the second monomer pair, and wherein the binary encoded polymer encodes the text or image or video or audio format.

According to one aspect, a method of translating a binary encoded nucleic acid from a nucleic acid sequence to a sequence of binary information bits representative of text or an image or a video or an audio format wherein adenine and thymine or uracil represents a first binary information bit and cytosine and guanine represent a second binary information bit is provided including the steps of reading the nucleic acid sequence and assigning the first binary information bit to each of adenine or more than one adenine when in series, assigning the first binary information bit to each of thymine or more than one thymine when in series, assigning the first binary information bit to each of uracil or more than one uracil when in series, assigning the second binary information bit to each of cytosine or more than one cytosine when in series, and assigning the second binary information bit to each of guanine or more than one guanine when in series, wherein the nucleic acid sequence includes at least one of two or more adenine in series, two or more thymine in series, two or more uracil in series, two or more cytosine in series or two or more guanine in series.

According to one aspect, a method of encoding and decoding text or an image or a video or an audio format is provided including the steps of converting the text or image or video or audio format into a plurality of bit sequences of a bit stream, designing a nucleic acid sequence corresponding to the plurality of bit sequences of the bit stream by assigning adenine or thymine to a first binary information bit and cytosine or guanine to a second binary information bit, wherein the assigning of adenine or thymine is alternated when the same binary information bit occurs directly in series, wherein the assigning of cytosine or guanine is alternated when the same binary information bit occurs directly in series, synthesizing the nucleic acid sequence, storing the synthesized nucleic acid sequence, reading the synthesized nucleic acid sequence, and decoding the synthesized nucleic acid sequence into the plurality of bit sequences of the bit stream by assigning the first binary information bit to either adenine or thymine and by assigning the second binary information bit to either cytosine or guanine. According to one aspect, the synthesized nucleic acid sequence includes at least one homopolymer of adenine, thymine, cytosine or guanine and wherein the decoding of the synthesized nucleic acid sequence includes assigning the first binary information bit to either a homopolymer of adenine or thymine or assigning the second binary information bit to either a homopolymer of cytosine or guanine.

According to one aspect, a method of storing information on a substrate using nucleic acid sequences representative of a plurality of bit sequences of a bit stream encoding for text or an image or a video or an audio format is provided including the steps of providing a substrate having single stranded nucleic acid initiator sequences attached thereto to regions on the array, contacting one or more locations with a template independent polymerase, a selected natural nucleotide, and one or more of $Co^{2+}$, $Mn^{2+}$, $Zn^{2+}$ and $Mg^{2+}$, catalyzing addition of the selected natural nucleotide to a 3' hydroxyl terminus of a target single stranded nucleic acid initiator sequence at the one or more locations, and repeating the step of catalyzing addition of selected natural nucleotides to produce a plurality of predetermined sequences at known locations of the substrate, wherein the plurality of predetermined sequences is representative of the plurality of bit sequences of the bit stream encoding for the text or the image or the video or the audio format. According to one aspect, the steps of catalyzing and repeating are carried out in series at a plurality of locations on the substrate to produce a plurality of predetermined sequences at known locations of the substrate. According to one aspect, the steps of catalyzing and repeating are carried out simultaneously at a plurality of locations on the substrate to produce a plurality of predetermined sequences each at corresponding known locations of the substrate to produce an array of predetermined sequences at corresponding known locations. According to one aspect, one or more of the plurality of predetermined sequences are sequenced and the sequence is translated into binary bit information which is then translated into the text or the image or the video or the audio format. According to one aspect, the substrate includes at least 102, 103, 104, 105, 106, 107, 108, 109, 1010 predetermined sequences each at corresponding known regions. According to one aspect, the predetermined sequences are greater than 100 nucleotides, 500 nucleotides, or 1000 nucleotides in length. According to one aspect, the template independent polymerase is terminal deoxynucleotidyl transferase. According to one aspect, the extension products of the natural nucleotides are produced by limiting reaction time of the natural nucleotide wherein nucleotide depleted buffer is added to remove the natural nucleotide thereby limiting its reaction time or where pulse rate of flow of the natural nucleotide across the surface of the substrate limits its reaction time at a particular desired location.

According to one aspect, a method of translating a binary encoded nucleic acid from a nucleic acid sequence to a sequence of binary information bits wherein adenine and thymine or uracil represents a first binary information bit and cytosine and guanine represent a second binary information bit is provided including the steps of reading the nucleic acid sequence and assigning the first binary information bit to each adenine or more than one adenine when in series, assigning the first binary information bit to each thymine or more than one thymine when in series, assigning the first binary information bit to each uracil or more than one uracil when in series, assigning the second binary information bit to each cytosine or more than one cytosine when in series, and assigning the second binary information bit to each guanine or more than one guanine when in series.

According to one aspect, an information storage device is provided containing stored information and including a substrate and a plurality of nucleic acid sequences disposed thereon wherein the plurality of nucleic acid sequences encode a series of binary information bits corresponding to the stored information and wherein adenine or a series of adenine, thymine or a series of thymine and uracil or a series of uracil represent a first binary information bit and wherein cytosine or a series of cytosine and guanine or a series of guanine represent a second binary information bit.

According to one aspect, a method of storing information using nucleotides is provided including the steps of converting a format of information into a plurality of bit sequences of a bit stream with each having a corresponding bit barcode, converting the plurality of bit sequences to a plurality of corresponding oligonucleotide sequences using one bit per base encoding, synthesizing the plurality of corresponding oligonucleotide sequences by pulsing and synchronizing reagents and washes across the surface of a substrate having a plurality of reaction locations, and storing the synthesized plurality of corresponding oligonucleotide sequences. According to one aspect, the oligonucleotide sequences include one or more or all of a data block sequence, an address sequence specifying the location of the data block in the bit stream, or flanking common sequences at each end of the oligonucleotide for amplification and sequencing.

According to one aspect, a method of retrieving a format of information from a plurality of synthesized oligonucleotide sequences encoding bit sequences of the format of information is provided including the steps of amplifying the plurality of oligonucleotide sequences, sequencing the amplified oligonucleotide sequences, converting the oligonucleotide sequences to bit sequences by interpreting homopolymer runs as a single nucleotide, and converting the bit sequences to the format of information. According to one aspect, the oligonucleotide sequences include one or more or all of a data block sequence, an address sequence specifying the location of the data block in the bit stream, or flanking common sequences at each end of the oligonucleotide for amplification and sequencing.

According to one aspect, a method of accessing a format of information from a plurality of synthesized oligonucleotide sequences encoding bit sequences of the format of information is providing including the steps of amplifying the plurality of oligonucleotide sequences, sequencing the amplified oligonucleotide sequences, converting the oligonucleotide sequences to bit sequences by interpreting homopolymer runs as a single nucleotide, converting the bit sequences to the format of information, and outputting the format of information. According to one aspect, the oligonucleotide sequences include one or more or all of a data block sequence, an address sequence specifying the location of the data block in the bit stream, or flanking common sequences at each end of the oligonucleotide for amplification and sequencing.

According to one aspect, a method of storing information using nucleotides is provided including the steps of converting a format of information to a bit stream, encoding bit sequences into corresponding oligonucleotide sequences, synthesizing the oligonucleotide sequences by pulsing and synchronizing reagents and washes across the surface of a substrate having a plurality of reaction locations, sequencing the oligonucleotide sequences, decoding the oligonucleotide sequences into bit sequences by interpreting homopolymer runs as a single nucleotide, assembling the bit sequences into a bit stream and converting the bit stream into the format of information. According to one aspect, the oligonucleotide sequences include one or more or all of a data block sequence, an address sequence specifying the location of the data block in the bit stream, or flanking common sequences at each end of the oligonucleotide for amplification and sequencing.

According to one aspect, a method of storing information using nucleotides is provided including the steps of converting a first format of information to a first bit stream, encoding first bit sequences into corresponding oligonucleotide sequences, synthesizing the oligonucleotide sequences by pulsing and synchronizing reagents and washes across the surface of a substrate having a plurality of reaction locations, sequencing the oligonucleotide sequences, decoding the oligonucleotide sequences into second bit sequences by interpreting homopolymer runs as a single nucleotide, assembling the second bit sequences into a second bit stream and converting the second bit stream into a second format of information. According to one aspect, the oligonucleotide sequences include one or more or all of a data block sequence, an address sequence specifying the location of the data block in the bit stream, or flanking common sequences at each end of the oligonucleotide for amplification and sequencing.

The contents of all references, patents and published patent applications cited throughout this application are hereby incorporated by reference in their entirety for all purposes.

Other Embodiments

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference in their entirety for all purposes to the same extent as if each individual publication or patent application were specifically and individually indicated to be so incorporated by reference.

What is claimed is:

1. A method of creating a binary encoded polymer comprising repeatedly extending a growing polymer chain with
   (i) one or more than one of either a first monomer or a second monomer of a first monomer pair or
   (ii) one or more than one of either a first monomer or a second monomer of a second monomer pair, to produce an extension product,
   wherein the extension product represents a series of binary information bits corresponding to a bit stream translated from information in a format,
   wherein each monomer of the first monomer pair is representative of a first binary information bit,
   wherein each monomer of the second monomer pair is representative of a second binary information bit, and alternating between the first monomer and second monomer of a given monomer pair when monomers of the extension products are representative of the same binary information bit and occur directly in series,
   wherein the extension product includes at least one homopolymer of either the first monomer or the second monomer of the first monomer pair or at least one homopolymer of either the first monomer or the second monomer of the second monomer pair and
   wherein the binary encoded polymer encodes the information from the format.

2. The method of claim 1 wherein the polymer is a nucleic acid.

3. The method of claim 1 wherein the first monomer or the second monomer of the first monomer pair is a nucleotide.

4. The method of claim 1 wherein the first monomer or the second monomer of the second monomer pair is a nucleotide.

5. The method of claim 1 wherein the first monomer pair includes adenine (A) and thymine (T) or uracil (U).

6. The method of claim 1 wherein the second monomer pair includes cytosine (C) and guanine (G).

7. The method of claim 1 wherein the extension products are formed using an enzyme and a selected monomer under conditions to catalyze addition of the selected monomer.

8. The method of claim 1 wherein the extension products are formed using a polymerase and a selected monomer under conditions to catalyze addition of the selected monomer.

9. The method of claim 1 wherein the extension products are formed using a template independent polymerase and a selected monomer under conditions to catalyze addition of the selected monomer.

10. The method of claim 1 wherein the growing polymer chain is attached to a substrate.

11. The method of claim 1 including a plurality of growing polymer chains formed from steps (i) and (ii).

12. The method of claim 1 including a plurality of growing polymer chains formed from steps (i) and (ii) and wherein the plurality of growing polymer chains is attached to a substrate.

13. The method of claim 1 wherein the first monomer or the second monomer of the first monomer pair is a natural nucleotide.

14. The method of claim 1 wherein the first monomer or the second monomer of the second monomer pair is a natural nucleotide.

15. The method of claim 1 wherein the first and second monomer pairs include natural nucleotides and the extension product is made by catalyzing the addition of a natural nucleotide under conditions sufficient to add a single nucleotide or more than one nucleotide.

16. The method of claim 1 wherein the first and second monomer pairs include natural nucleotides and the extension product is made by alternating at one or more locations on a substrate administration of a polymerase and a selected nucleotide with a nucleotide deficient buffer and thereby catalyzing the addition of a natural nucleotide under conditions sufficient to add the nucleotide.

17. The method of claim 1 wherein the format of information is a text or image or video or audio format.

\* \* \* \* \*